United States Patent [19]

Covey et al.

[11] Patent Number: 5,206,415
[45] Date of Patent: Apr. 27, 1993

[54] TRICYCLIC STEROID ANALOGS

[75] Inventors: Douglas F. Covey, Ballwin; Yuefei Hu; Charles F. Zorumski, both of St. Louis, all of Mo.

[73] Assignee: Washington University, St. Louis, Mo.

[21] Appl. No.: 811,208

[22] Filed: Dec. 20, 1991

[51] Int. Cl.⁵ .......................................... C07C 69/608
[52] U.S. Cl. .................................. 560/117; 568/373; 568/817; 564/459; 558/429; 560/256; 562/499
[58] Field of Search ............... 568/373, 817; 560/117, 560/256; 584/459; 558/429; 562/499

[56] References Cited

U.S. PATENT DOCUMENTS

| | | | |
|---|---|---|---|
| 2,830,075 | 4/1958 | Farinacci | 568/373 |
| 3,499,913 | 3/1970 | Joly et al. | 568/373 |
| 3,676,461 | 7/1972 | Muller et al. | 568/373 |
| 3,821,288 | 6/1974 | Crabbe et al. | 568/373 |
| 4,874,891 | 10/1989 | Covey et al. | 568/373 |

FOREIGN PATENT DOCUMENTS 2068363 8/1981 United Kingdom .
8902272 8/1987 World Int. Prop. O. .

OTHER PUBLICATIONS

Phillipps et al., in Molecular Mechanisms in General Anesthesia, Eds. Halsey et al., Churchill Livingston, N.Y. 1974, pp. 32-47.
Majewska, Biochem. Pharmacal. 36, 3781-3788 (1987).
Metcalf et al., TIPS 10, 491-495 (1989).
The Merck Index, 11th ed., 1989, No. 6280.
Villotti et al., J. Am. Chem. Soc., 82, 5693-5700 (1960).
Capsi & Balasubrahanyam, Tetrahedron Lett. 12, 745-748 (1963).
Cross et al., J. Med. Chem. 6, 162-166 (1963).

*Primary Examiner*—James H. Reamer
*Attorney, Agent, or Firm*—Scott J. Meyer

[57] ABSTRACT

Novel tricyclic steriod analogs are disclosed which are 1H-benz[e]indene dodecahydro compounds that are useful for enhancing GABA-induced chloride currents at the GABA receptor/chloride ionophore complex and can be represented by the following structural formulas:

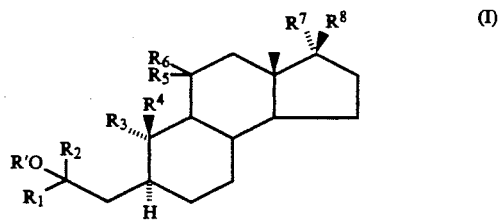

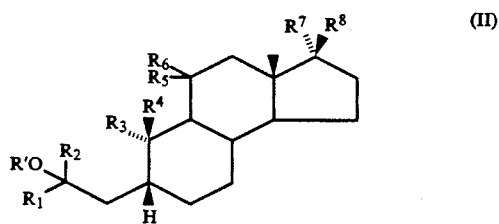

wherein
$R_1$ = H or $C_1$-$C_4$ alkyl or fluoroalkyl;
$R_2$ = H or $C_1$-$C_4$ alkyl or fluoroalkyl, in which $R_1$ and $R_2$ can be the same or different;
$R_3$ = H or $CH_3$;
$R_4$ = H or $CH_3$, in which $R_3$ and $R_4$ can be the same or different;
$R_5$ = H;
$R_6$ = H;
$R_5, R_6$ ==O(carbonyl);
$R_7$ = H;
$R_8$ = a hydrogen bond accepting group.
$R_7, R_8$ ==O(carbonyl); and
$R'$ = an ester group.

10 Claims, 1 Drawing Sheet

TRICYCLIC STEROID ANALOGS

ACKNOWLEDGEMENT OF SUPPORT

The invention herein was made in part with government support under NIH grants HD19746 and NS14834. The government has certain rights in the invention.

BACKGROUND OF THE INVENTION

This invention relates to novel tricyclic steroid analogs. More particularly, the invention relates to 1H-benz[e]indene dodecahydro compounds that are useful for enhancing gamma-aminobutyric acid (GABA)-induced chloride currents at the GABA receptor/chloride ionophore complex.

The importance of steroids as crucial components of cellular membranes is well established. Equally well established are the long term endocrine effects of steroid hormones. These endocrine effects are due to binding of steroids to intracellular receptors that subsequently interact with DNA and modulate gene expression. Less well delineated, but currently the subject of increasing interest, are the immediate modulatory effects of certain steroids at ion channels. For example, it is now established that steroid anesthetics, as well as certain endogenously produced metabolites of progesterone and deoxycorticosterone, facilitate GABA's ability to increase neuronal inhibition (for reviews see refs. 10, 15, 25). These steroid effects on GABAergic function have significant pharmacological, physiological, and pathological implications.

GABA is thought to be the major inhibitory neurotransmitter in the vertebrate central nervous system (CNS), exerting actions at two classes of receptors, designated $GABA_A$ and $GABA_B$. These receptors can be distinguished physiologically and pharmacologically (5). $GABA_B$ sites represent the minority of CNS GABA receptors and, based on available studies, are unlikely to be a primary site of action for anesthetic/anticonvulsant drugs. In contrast, $GABA_A$ receptors appear to represent a major site of action for many CNS-active agents and are thought to be a site at which several classes of anesthetics exert their effects. At $GABA_A$ receptors, GABA promotes the direct opening of $Cl^-$-selective ion channels. In most neurons, based on electrochemical gradients, the opening of these channels promotes the influx of $Cl^-$ and produces hyperpolarization of the neuronal membrane. A recurring theme in the GABA literature is that drugs which inhibit $GABA_A$ function, including the competitive antagonist bicuculline and the non-competitive antagonists picrotoxin, t-butylbicyclophosphorothionate (TBPS) and penicillin, act as convulsants whereas agents which augment GABA function, including benzodiazepines and barbiturates, act as anticonvulsants, anesthetics and sedatives (for review see ref. 49).

Consistent with Selye's (42) initial observations that steroids have CNS depressant properties, studies done over the past decade have provided evidence that the anesthetic actions of steroids may occur through enhancement of $GABA_A$-mediated neuronal inhibition. Initial studies demonstrated that alphaxalone, an anesthetic steroid, prolongs the time course of GABA-mediated inhibitory synaptic responses in olfactory cortical slices (39). Subsequent studies using voltage clamp and single channel recording techniques have provided clear evidence that both anesthetic and endogenous steroids can alter $GABA_A$ receptor function in a variety of preparations. In cultured rat hippocampal and spinal cord neurons, anesthetic steroids augment $Cl^-$ currents produced by exogenous GABA (3, 24). Additionally, alphaxalone has been shown to open $Cl^-$ channels directly in the absence of GABA, at concentrations which are relevant to anesthetic effects (3). These steroid gated currents are blocked by bicuculline, suggesting that they are mediated through direct activation of $GABA_A$ receptors, perhaps by an action at the GABA recognition site. In addition to potentiating responses to exogenous GABA, alphaxalone augments inhibitory postsynaptic currents (IPSCs) mediated by $GABA_A$ receptors in cultured hippocampal neurons (14). This effect is manifest as a 5–8 fold prolongation of IPSC decay without change in peak IPSC amplitude or rise time. Taken together, these studies strongly suggest that both by direct $Cl^-$ channel activation and by modulation of GABA-mediated responses anesthetic steroids augment neuronal inhibition through modulation of the $GABA_A$ receptor complex.

The site at which steroids exert these effects remains unclear. Certain actions, including the direct gating of $Cl^-$ channels and the prolongation of IPSC decay are similar to the effects of anesthetic barbiturates (40). In addition, fluctuation analysis experiments have shown that alphaxalone, like the barbiturates, significantly prolongs the burst length of GABA-gated channels without changing the single channel conductance (3). However, recent studies using single channel recordings from recombinant human $GABA_A$ receptors expressed in human embryonic kidney cells have found differences in the actions of barbiturates and endogenous steroid metabolites. Whereas pentobarbital prolongs channel open times and burst lengths, $3\alpha$-OH-dihydroprogesterone (DHP) increases the frequency of channel opening without altering the open times (35). Other studies using ligand binding and $Cl^-$ flux measurements have demonstrated additive and synergistic effects of barbiturates and steroids, suggesting separate sites of action (11, 19, 47). Additionally, in bovine adrenal chromaffin cells, steroids greatly potentiate currents induced by high concentrations of pentobarbital (6). This suggests that either steroids and barbiturates act at separate sites in the $GABA_A$ complex or that the effects on GABA-gated responses are mediated by a site that is distinct from the site mediating direct $Cl^-$ channel gating.

An action of steroids at benzodiazepine receptors is less likely as several studies have failed to find an effect of the benzodiazepine antagonist R015-1788 (flumazenil) on steroid responses (6, 29). Additionally, benzodiazepine agonists potentiate GABA responses by increasing the apparent affinity of GABA for its receptor (7) without altering the single channel properties of the current (45). Benzodiazepine agonists also increase both the duration and amplitude of GABA-mediated IPSCs, an effect which differs from either the steroids or barbiturates (41). Finally, unlike steroids or barbiturates, benzodiazepines do not appear to gate $Cl^-$ channels directly in the absence of GABA.

Further complicating attempts to define the steroid site of action are observations that some steroid analogs inhibit GABA responses. Both pregnenolone sulfate (PS) and dehydroepiandrosterone sulfate (DHEAS) inhibit GABA currents in various CNS neurons (22, 23). However, PS, but not DHEAS, inhibits TBPS binding at the picrotoxin site, suggesting that these two agents may act at separate loci to affect GABA responses. Additionally, PS and picrotoxin have similar single channel effects, decreasing the opening frequency of the channels (27). These observations raise the possibility that the picrotoxin site may be responsible for some steroid actions. Previous studies using alkyl substituted γ-butyrolactones have shown that both potentiation and inhibition of $GABA_A$ responses can be produced by agents acting at the picrotoxin site (16, 17). Interestingly, the 7-butyrolactones appear to alter GABA currents by changing the frequency of channel opening with less effect on the channel open times and no effect on the single channel conductance (2, 48).

Based on the data outlined above, it is clear that anesthetic and endogenous steroids can modulate $GABA_A$ receptor function. However there are several possibilities for the site(s) of action within the complex. The direct $Cl^-$ channel gating may be produced through an action at the GABA recognition site, based on the bicuculline sensitivity of the response. The alteration of responses produced by exogenous GABA and of IPSCs is more likely mediated through an allosteric site. Currently the putative barbiturate and picrotoxin sites are the leading candidates.

Steroid anesthetics were developed by the pharmaceutical industry decades before their effects at GABAergic neurons were established. The steroid anesthetic preparation, Althesin, was considered by anesthesiologists in Europe to have many of the properties desired for an intravenous anesthetic. These favorable properties have been discussed in an editorial by Morgan and Whitman (28). These authors also noted that Althesin was particularly effective and safe for use as an anesthetic in patients with high intracranial pressure resulting from severe head trauma. Unfortunately, Althesin is no longer available to anesthesiologists. It was removed from clinical use because of allergic reactions caused by the solubilizing agent used in the formulation.

Majewska has reviewed the role that steroid modulators of GABAergic function could play in the response to stress (25). Stress causes the release of CRF (corticotropin-releasing factor) from the hypothalamus. CRF in turn causes the release of adrenocorticotropic hormone (ACTH) from the pituitary, and ACTH then stimulates adrenal steroid biosynthesis. Among the adrenal steroids produced are cortisol and deoxycorticosterone. Cortisol has been shown to have biphasic actions at the GABA receptor channel complex found in guinea pig ileum (31). In picomolar concentrations it augments GABA-induced chloride currents, but at nanomolar concentrations it inhibits these same currents. Recent studies (36) support the hypothesis that the elevated concentrations of cortisol resulting from stress-induced increases in ACTH secretion could diminish neuronal inhibition by GABA and enhance the arousal state brought on by stress. Majewska further postulates that these effects may be enhanced by yet another endogenous steroid, pregnenolone sulfate, that she has shown to inhibit GABA-induced chloride currents (22). This sulfated steroid can be made not only in peripheral organs, but also by glial cells in the central nervous system (for a review of brain steroid biosynthesis see ref. 4). Finally, Majewska postulates that the deoxycorticosterone also released from the adrenal gland during stress has an important physiological function. Since deoxycorticosterone can be metabolized to THDOC (5α-pregnane-3α, 21-diol-20-one), a steroid known to augment GABA-mediated neuronal inhibition (22), this steroid is postulated to counteract the effects of cortisol at the GABA receptor channel complex and restore homeostasis to the brain during stress.

This ability of endogenous steroids to either decrease or increase GABA-mediated neuronal inhibition has led many investigators (15, 20, 21, 25) to postulate that new steroid derivatives might be useful not only as anesthetics, but also as sedative hypnotics, anxiolytics, anticonvulsants, and antidepressants. In support of these potential uses for synthetic steroid derivatives that could modulate GABAergic function are the following results: 1) THDOC has shown both anxiolytic and sedative activity (different dose/repose curves) in two different animal models of anxiety (8); 2) THDOC has been shown to induce sleep and increase nonREM sleep in rats (26); 3) Saffan (a veterinary formulation of anesthetic steroids) at doses causing neurological symptoms, has been shown to have anticonvulsant activity against both maximal electroshock and chemically-induced seizures (33); and 4) depression is a frequent condition encountered in patients with Cushing's syndrome and it can be treated by lowering the elevated cortisol levels found in these patients (30).

The progesterone metabolite, 3α-OH-DHP (3α-hydroxy-5α-pregnan-20-one), shown below, is also thought to be an important physiologic regulator of GABA-mediated neuronal inhibition. This compound can be made de novo in brain or produced there from circulating progesterone (4). The observation that women having catamenial epilepsy, a condition in which seizure frequency changes during the menstrual cycle, have more seizures when progesterone levels are low during the menstrual cycle has led to the hypothesis that compounds mimicking the actions of 3α-OH-DHP may be useful as anticonvulsants and treatments for premenstrual syndrome (38). The later hypothesis is further supported by the fact that progesterone is often useful for treating premenstrual symdrome (25).

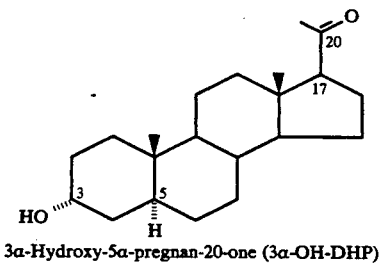

3α-Hydroxy-5α-pregnan-20-one (3α-OH-DHP)

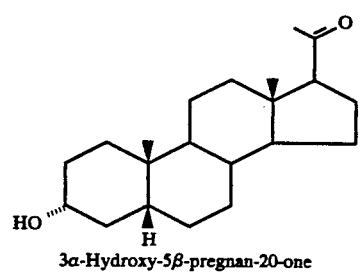

3α-Hydroxy-5β-pregnan-20-one

In summary, the effects of steroid modulation of GABA receptor channel function are highly significant. Steroid-induced hyperpolarization of GABAergic neurons is most likely the mechanism of action of anesthetic steroids. In addition, endogenously produced steroid metabolites of deoxycorticosterone and progesterone may be important physiological modulators of GABA-regulated neuronal inhibition.

Further background information on the structure/activity relationships in steroidal anesthetics can be had by reference to the review article by Phillips (34). Both of the above illustrated compounds, 3α-hydroxy-5α-pregnan-20-one and 3α-hydroxy-5β-pregnan-20-one, are active in vivo as steroid anesthetics according to Phillips. These compounds also are potentiators of muscimol-stimulated chloride uptake in rat synaptoneurosomes (37) and potentiators of GABA-induced chloride currents in electrophysiological experiments (13, 32).

BRIEF DESCRIPTION OF THE INVENTION

In accordance with the present invention, novel tricyclic steroid analogs are provided which are 1H-benz[e]indene dodecahydro compounds. For convenience of presentation, the numbering system and nomenclature rules associated with steroids instead of benz[e]indenes are used herein for description of the invention. Accordingly, these compounds can be represented by the following structural Formulas I and II in the 5α- and 5β-configurations (7α- and 7β-configurations according to the benz[e]indene numbering system), respectively:

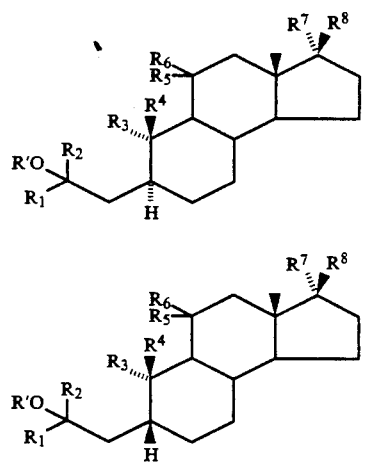

wherein
$R_1$=H or $C_1$-$C_4$ alkyl or fluoroalkyl;
$R_2$=H or $C_1$-$C_4$ alkyl or fluoroalkyl, in which $R_1$ and $R_2$ can be the same or different;
$R_3$=H or $CH_3$;
$R_4$=H or $CH_3$, in which $R_3$ and $R_4$ can be the same or different;
$R_5$=H;
$R_6$=H;
$R_5,R_6$==O(carbonyl);
$R_7$=H;
$R_8$=a hydrogen bond accepting group.
$R_7,R_8$==O(carbonyl); and
R'=an ester group.

In the above Formula I and II, the preferred hydrogen bond accepting groups are as follows:
1) ketones (—CO—R", where R" can be alkyl or fluoroalkyl groups $C_1$ to $C_4$ or cycloalkyl groups $C_3$ to $C_6$.
2) an α-hydroxy ketone (—CO—CH$_2$OH) or esters thereof (—CO—CH$_2$OXOR''', where X=C, P=O-

(OR'''), or S=O; where R'''' can be alkyl groups $C_1$ to $C_{20}$).
3) alkyl esters of carboxylic acids (—COOR''', —CH$_2$COOR''', where R''' can be alkyl groups $C_1$ to $C_{20}$).
4) amines (NHR'' and N(R'')$_2$ where R'' can be alkyl or fluoroalkyl groups $C_1$ to $C_4$ or cycloalkyl groups $C_3$ to $C_6$).
5) a nitrile (CN)
6) a γ-lactone

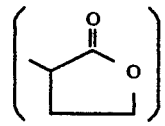

The ester group (R') can be any group derived from reaction between the hydroxyl group with a $C_1$-$C_{18}$ organic acid, acid halide, anhydride, or ester, such as, e.g., acetic, propionic, n- and i-butyric, n-, i-, s-, and t-valeric, hexanoic, heptanoic, octanoic, nonanoic, decanoic, undecanoic, dodecanoic, palmitic, stearic, cinnamic, benzylic, benzoic, maleic, fumaric, ascorbic, succinic, oxalic, tartaric, citric, fluconic, itaconic, aspartic, and the like.

The preferred configuration is the 5α-configuration of Formula I.

The most preferred compounds of Formula I are the four compounds which can be represented by the following structural Formula III:

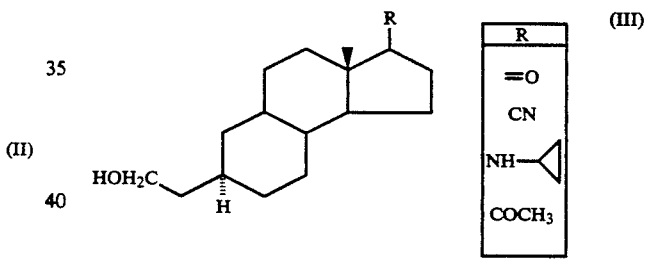

These novel 1-H-benz[e]indene dodecahydro compounds have been biologically evaluated on currents gated by 1 μM GABA, and the responses compared to effects produced by a 3α-OH-DHP, a neurosteroid known to augment GABA responses. These compounds exhibit reversible GABA potentiating effects at 1 μM and three of the preferred four compounds enhance GABA currents to a greater extent than 3α-OH-DHP.

The compounds of the invention are useful for treating disorders which can be ameliorated by increasing neuronal inhibition via modulation of GABA-regulated chloride channels. Thus, the compounds have utility as anxiolyotics, anticonvulsants, sedative hypnotics, and agents to treat premenstrual syndrome. The compounds may also be useful as anesthetics. The compounds are formulated according to conventional methods, and may be administered systematically by injection subcutaneously, intravenously, or intraperitoneally, as well as by oral or transdermal administration. The pharmaceutical compositions containing these compounds will, of course, depend on the route of administration.

Parenteral administration is generally characterized by injection, whether subcutaneously, intramuscularly, or intravenously. Injectables can be prepared in conventional forms, either as solutions or suspensions, in solid forms suitable for solution or suspension in liquid prior to injections or as emulsions. Suitable excipients include water, saline, dextrose, glycerol, and the like. If desired, the pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain about 10–95% active ingredient with the remainder carrier, as a general rule.

For administration via suppository, conventional binders and carriers include, for example, polyalkylene glycols or triglycerides, and the suppositories generally contain active ingredient in the range of about 0.5–10%. Standard methods of formulating compounds for administration as pharmaceuticals can be found in Remington's Pharmaceutical Sciences, Mack Publishing Company, Easton, Pa., latest edition.

The amount of active compound to be administered depends on the subject being treated, the severity of the condition being treated, the manner of administration, and the judgment of the physician. However, an effective dose is in the range of about 0.5–500 mg/day per typical subject.

DETAILED DESCRIPTION OF THE INVENTION

Figure 1:
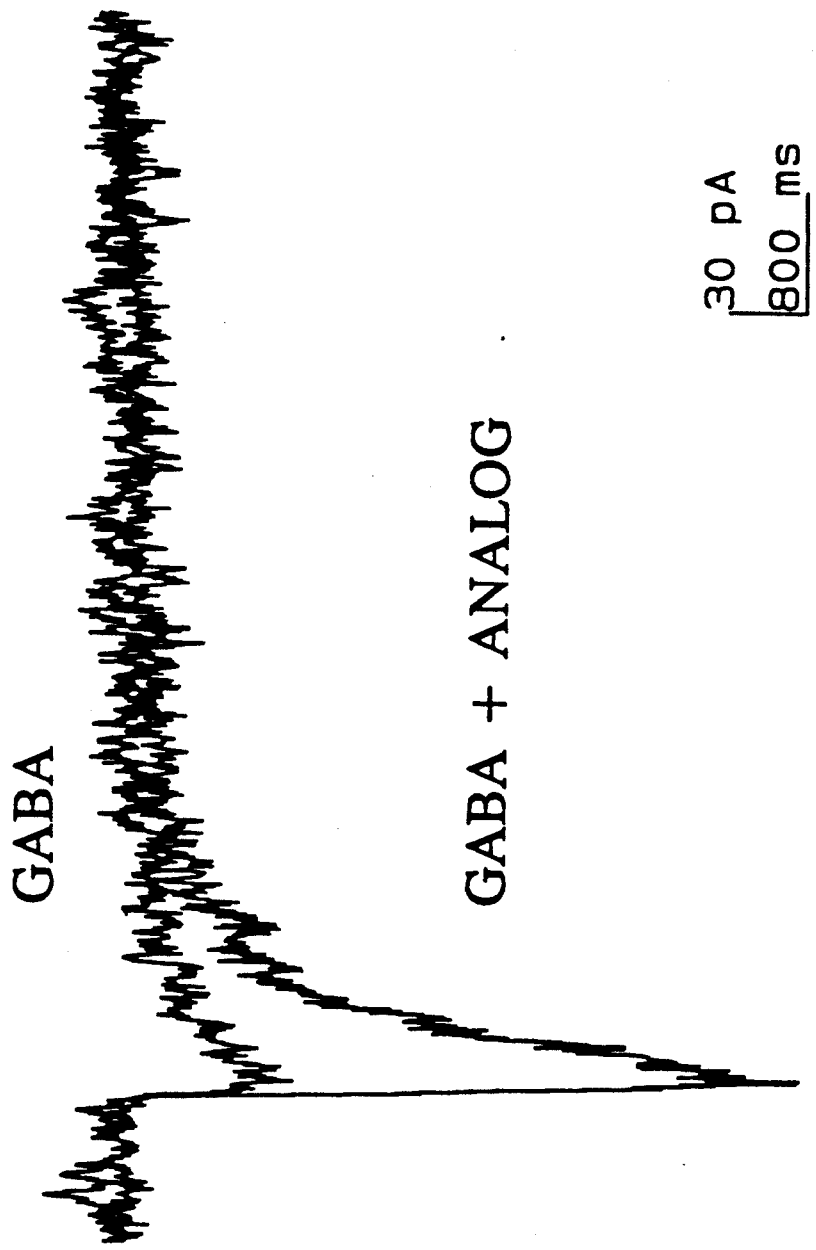

While the specification concludes with claims particularly pointing out and distinctly claiming the subject matter regarded as forming the invention, it is believed that the invention will be better understood from the following description of preferred embodiments taken in conjunction with the accompanying drawing in which:

FIG. 1 shows the modulation of GABA currents by a representative example of the tricyclic steroid analogs of the invention. Shown is the effect of the analog prepared in Example 13 and Table 1, below, in which R=COCH$_3$ on currents induced by 1 μM GABA. Neurons were voltage clamped at −5omV, and the test compound administered at 1 μM.

The synthesis of the preferred compounds of generic Formulas I and II is conveniently shown in the following Reaction Schemes 1 and 2. The synthetic method in Reaction Scheme 1 comprises a series of steps to open the A-ring of the known and readily available steroid, 19-nortestosterone, and remove the C$_1$ and C$_2$. The lithium, liquid ammonia reaction carried out in the first step yields the 5α-configuration at the A/B ring fusion (9). Each of the steps carried out in Reaction Scheme 1 is carried out in high yield. Whenever more than one transformation is indicated on an arrow between structures, the yield reported is the overall yield for the combined transformations. EAch of the compounds shown in the Reaction Scheme 1 has been purified to homogeneity by chromoatographic methods. These compounds have been shown to have the correct elemental composition by combustion analysis and have been characterized by infrared and NMR spectroscopy.

Scheme 1

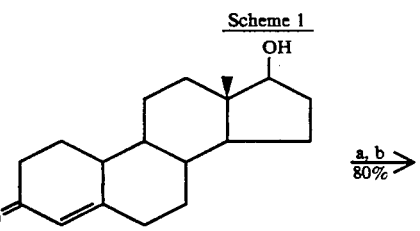

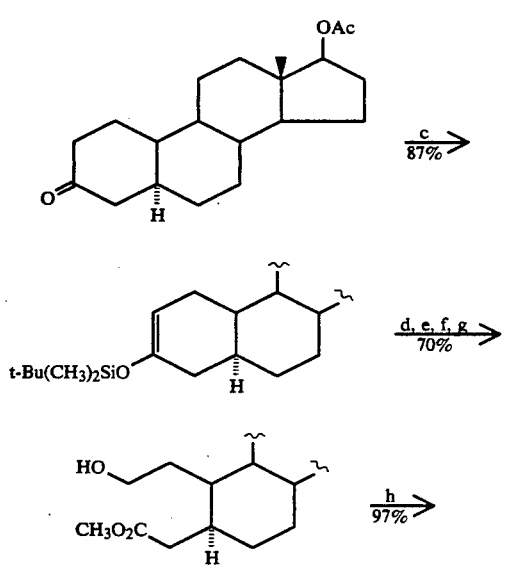

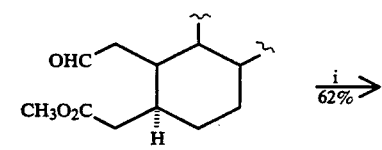

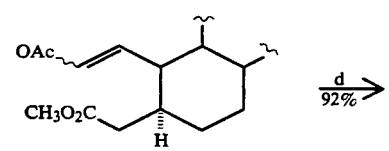

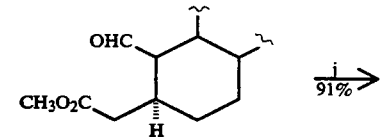

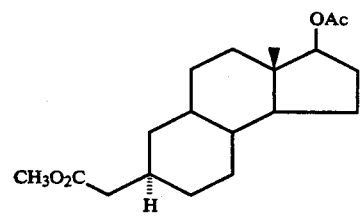

a) Li, liq. NH$_3$;  b) Ac$_2$O, Pyr, 100° C.;  c) t-Bu(CH$_3$)$_2$SiOTf;
d) O$_3$, CH$_3$OH, CH$_2$Cl$_2$, −78° C.;  e) NaBH$_4$;
f) Na$_2$CO$_3$, aq. THF;  g) CH$_2$N$_2$, Et$_2$O;
h) PCC, NaOAc, CH$_2$Cl$_2$;  i) AcO(CH$_3$)C=CH$_2$, p-TsOH;
j) Wilkinson's cat., C$_6$H$_5$CN.

Reaction Scheme 2 details the remaining steps needed to preoare various 5α-analogs having the different hydrogen bond acceptor groups (i.e., C=O, CN, COCH$_3$, and cyclopropyl-NH group) of the final compounds. Yields shown under the arrows are yields obtained for the four preferred compounds whose evaluation are set forth in Table 1, hereinafter. The cyano group introduced in the TosMIC reaction (step c) is introduced with ca. 70% 17β-stereochemistry. The 17α-cyano isomer was removed by chromatography.

Finally, in order to synthesize the 5β-analogs, two additional steps not shown in Reaction Scheme 1 are carried out as shown below. The effect of these two steps is to change the side chain from the 5α-configuration to the 5β-configuration. The final comopund shown in Reaction Scheme 1 is converted by an α-phenylselenylation/elimination reaction into the α, β-unsaturated ester (43). Catalytic hydrogenation using palladium in tetrahydrofuran and hydrobromic acid is then carried out to give the 5β-reduced tricyclic analog. These conditions are analogous to the conditions

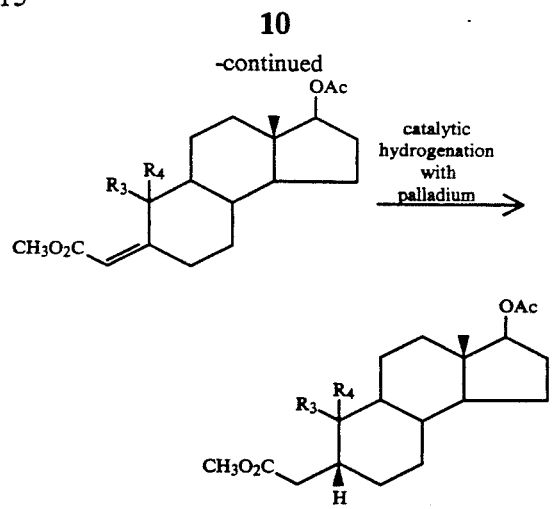

Scheme 2

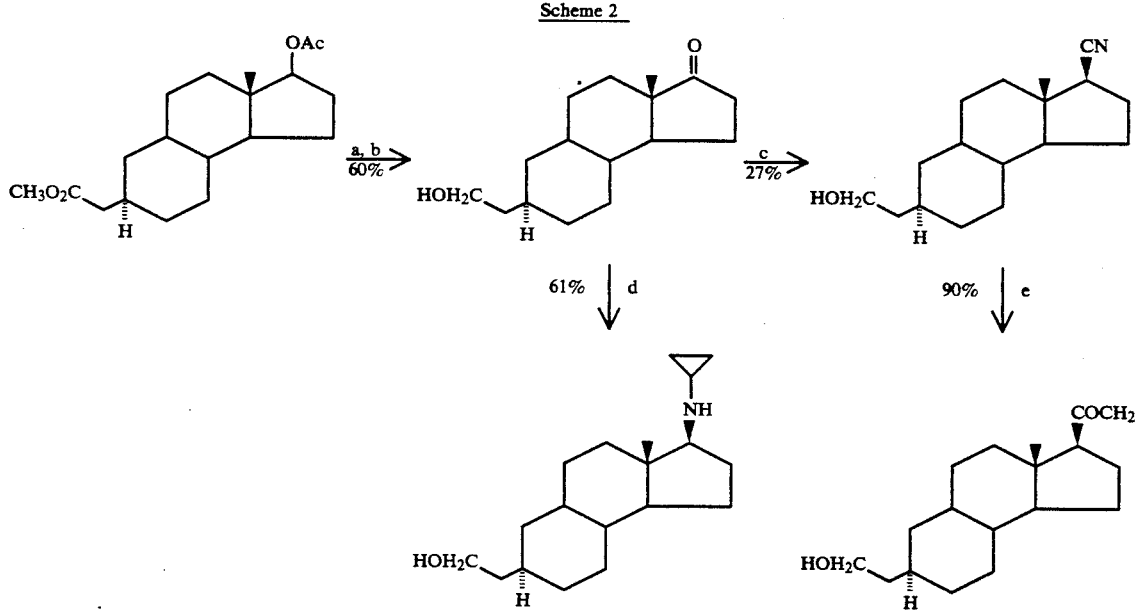

a) DIBAL-H, CH$_2$CH$_2$, 20°; b) NaOCl, HOAc; c) TosMIC, KOC(CH$_3$)$_3$, DME; d) cyclopropylamine, NaBH$_3$CN, CH$_3$OH; e) CH$_3$MgI, EtOEt.

known to convert 19-nortestosterone to 5β-dihydrotestosterone with 98% stereospecificity (46). Chromatographic methods can be used to separate mixtures of the 5α and 5β-compounds.

Additional tricyclic steroid analogs within the scope of Formulas I and II can be prepared by various of the following reaction schemes:

Introduction of R$_1$ and R$_2$ alkyl or fluoroalkyl groups where R$_1$=R$_2$ or R$_1$ not=R$_2$ can be prepared as follows:

Example 7

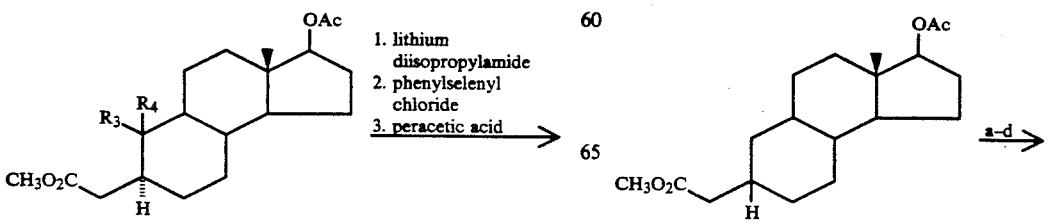

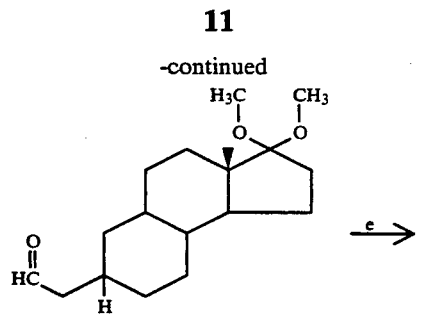

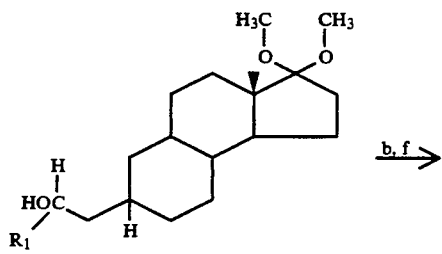

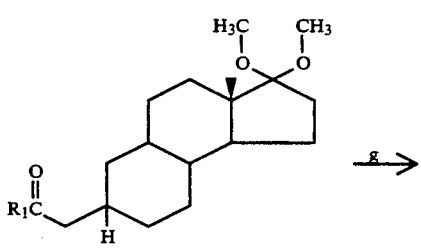

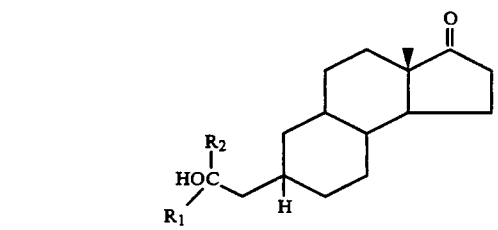

a) NaOH, aq. CH₃OH;
b) H₂CrO₄, acetone;
c) CH₃COCl, CH₃OH, 50° C.;
d) DIBAL-H, CH₂CH₂, −78° C.;
e) R₁MgBr or (CH₃)₃SiCF₃ (when R₁ = CF₃);
f) R₂MgBr;
g) acetone, aq. H₂SO₄.

Examples show preparation of compounds where R₃=R₄=H or R₃=H and R₄=CH₃ preparation of compounds where R₃=CH₃ and R₄=H or CH₃ is as follows:

Example 4, R₄ = H

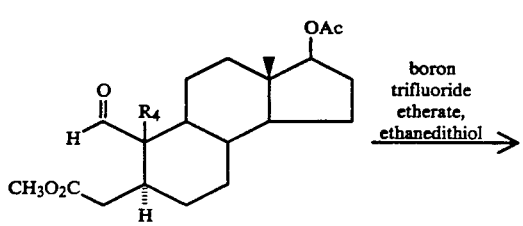

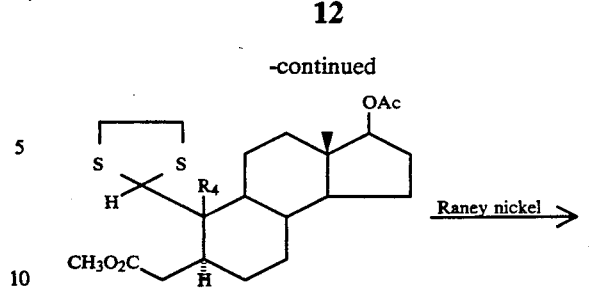

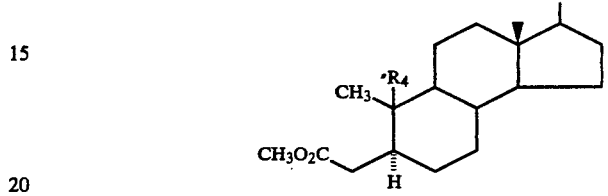

Compounds having R₅, R₆==O could be prepared by starting with materials having a ketone at the 11-position. For example:

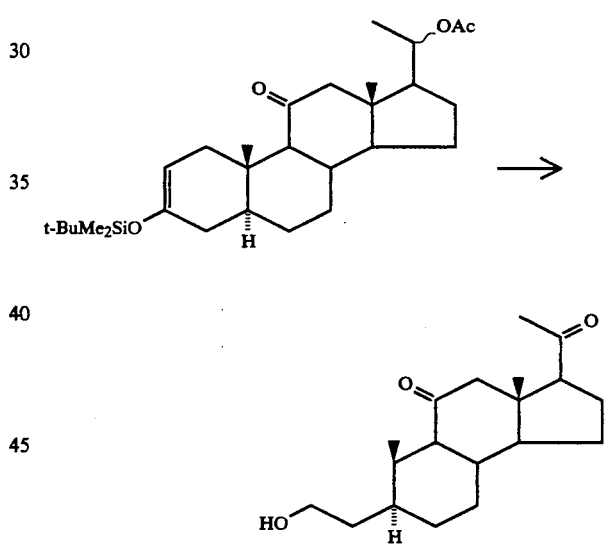

The α-hydroxyketones can be prepared from ketones as follows:

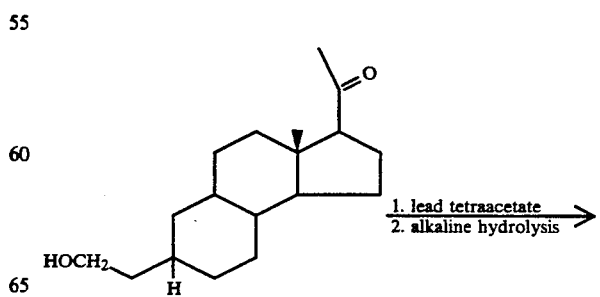

Example 13

13

-continued

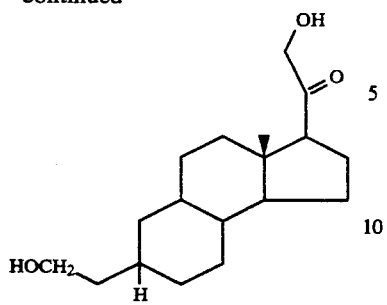

The various derivatives of the α-hydroxyketone are prepared as follows:

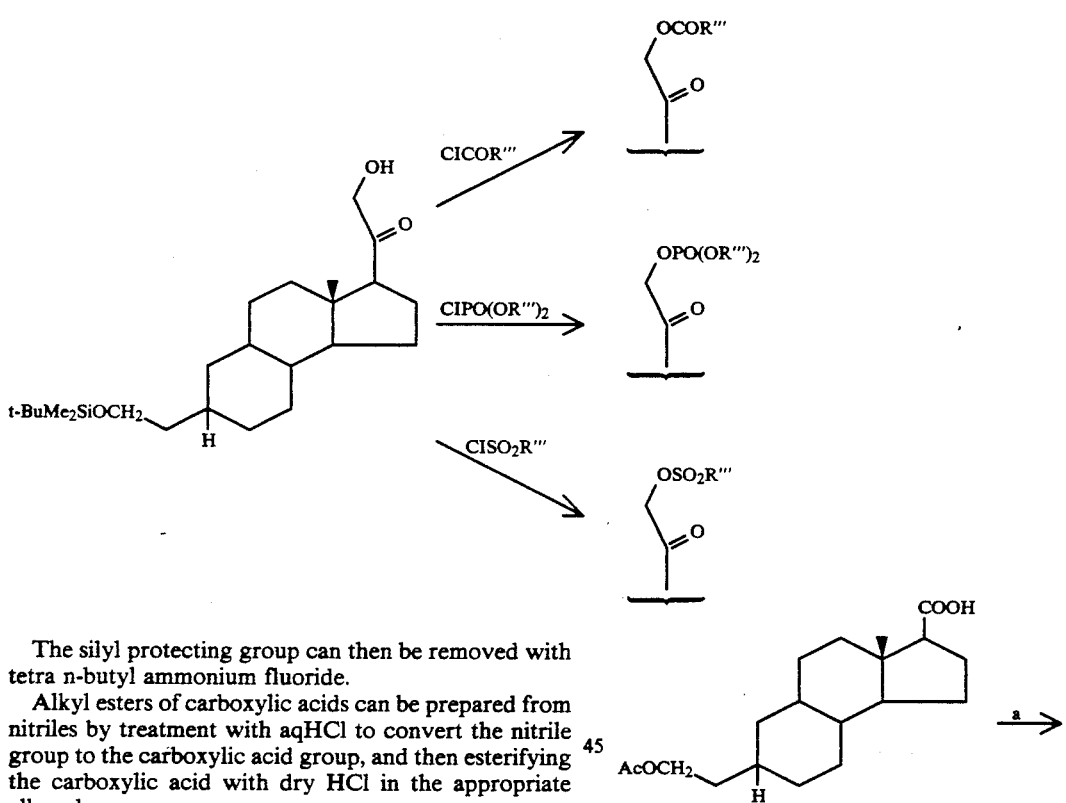

The silyl protecting group can then be removed with tetra n-butyl ammonium fluoride.

Alkyl esters of carboxylic acids can be prepared from nitriles by treatment with aqHCl to convert the nitrile group to the carboxylic acid group, and then esterifying the carboxylic acid with dry HCl in the appropriate alkanol.

14

-continued

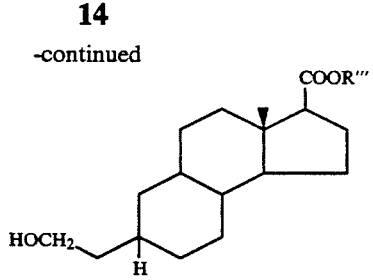

γ-Lactones can be prepared as follows:

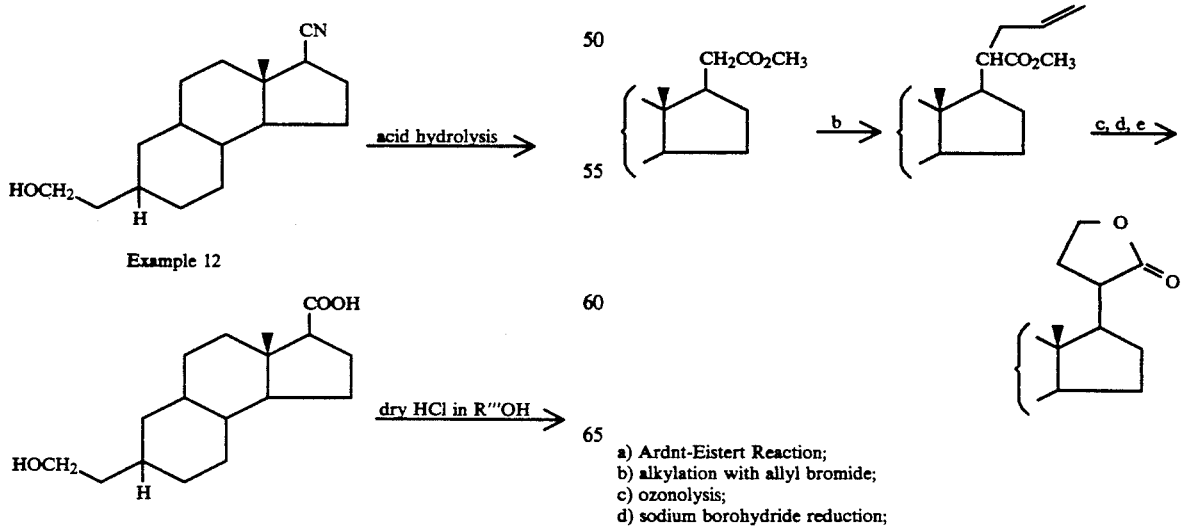

a) Arndt-Eistert Reaction;
b) alkylation with allyl bromide;
c) ozonolysis;
d) sodium borohydride reduction;

-continued e) acidification

The following detailed Examples will further illustrate the invention although it will be understood that the invention is not limited to these specific Examples or the details described therein.

As indicated in structural Formulas I and II, R4 can be H or CH3. The following are general structures of compounds prepared in the following specific examples in which R can be H or CH3.

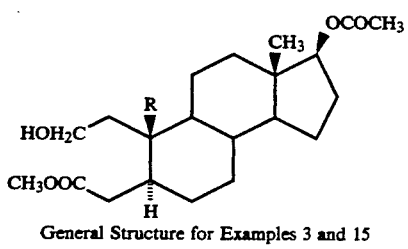

General Structure for Examples 3 and 15

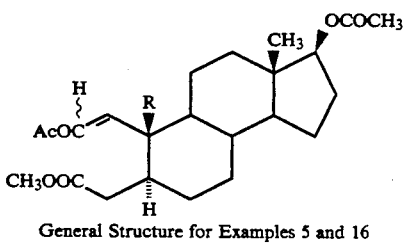

General Structure for Examples 5 and 16

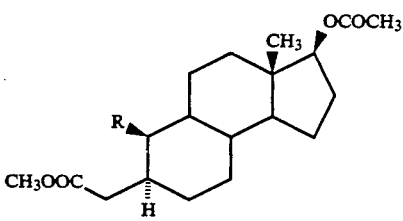

General Structure for Examples 7 and 17

EXAMPLE 1

Preparation of 3[[(1,1Dimethylethyl)dimethylsilyl]oxy]-5α-estran-17β-ol acetate

To a solution of 17β-acetyloxy-5α-estran-3-one (1.595 g, 5 mmol) in dry dichloromethane (30 mL) was added with stirring at ice-water bath temperature, triethyl amine (2 mL) followed by t-butyldimethylsily triflate (2.64 g, 10 mmol). The solution was stirred for 25 min, then diluted with dichloromethane (20 mL) and washed with satd.aq. NaHCO3 (30 mL), brine (30 mL) and dried over Na2SO4. The solvent was removed to yield a solid, which was purified by chromatography (silica gel, dichloromethane, pretreated with 1% triethyl amine in hexanes) to get 1.9 g (87%) to pure product as colorless crystals, m.p. 89°–90° C.

IR (film, NaCl): 2927, 2858, 1739, 1676, 1472, 1371, 1246 cm$^{-1}$.

$^1$H NMR (CDCl3): δ4.80 (dd, 1H, CH=C), 4.59 (dd, 1H, CHOAc), 2.04 (s, 3H,COCH3), 0.91 (s, 9H, (CH3)3C), 0.80 (s, 3H, CH3), 0.11 (s,6H, (CH3)2Si).

$^{13}$C NMR(CDCl3): δ171.58 (CH3COO), 149.88 (C36l), 103.48 (C2), 82.97 CH17), 25.51 ((CH3)3C), 11.81 (C18), −4.62 and −4.78 ((CH3)3CSi and (CH3)2Si).

Elemental Analysis: For C26H44O3Si. Calcd: C, 72.17; H, 10.25; Found: C, 72.49; H, 10.06.

Structure:

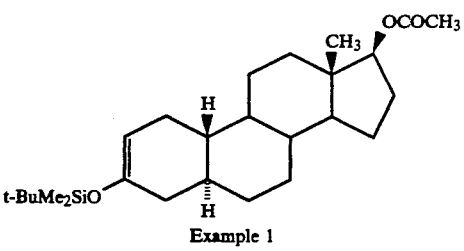

Example 1

EXAMPLE 2

Preparation of [3S-(3α,3aα,5aβ,6β,7α,9aα,9bβ)]-3-(Acetyloxy)-dodecahydro-6-(2-hydroxyethyl)-3a-methyl-1H-benz[e-]indene-7-acetic acid A solution of the silyl ether of Example 1 (0.866 g, 2 mmol) in dichloromethane (10 mL0 and methanol (10 mL) was treated with O3 at −78° C. until a blue color persisted. Excess O3 was discharged by O2 stream. NaBH4 (1.0 g) was added with stirring. The mixture was diluted with diethyl ether (25 mL) and poured into cooled 10% aq.HCl solution 250 mL). The organic phase was washed with water (25 mL), brine (25 mL), and dried over Na2SO4. The solvent was removed on a rotary evaporator to give a viscous liquid, which was diluted with n-hexane to give a colorless solid. Another portion of product was obtained by evaporting the n-hexane solution and hydrolyzing the residue with a mixture consisting of 10% aq. K2CO3 (10 mL), tetrahydrofuran (15 mL), and methanol (30 mL) for 1.5 h at room temperature. The crude compound was recrystallized from methanol to give 0.49 g (70%) pure compound as colorless crystals, m.p. 141°–145° C.

IR (film, NaCl):–3328, 2918, 1732, 1705, 1444, 1732, 1246 cm$^{-1a}$.

$^1$NMR (CDCl3): δ4.59 (t,J=8.4 Hz, 1H, CHOAc), 3.56–3.69 (m, 2H, CH2OH), 2.62 (dd,J=15.8,J=2.6 Hz, 1H of CH2COOH), 2.5 (s, 3H, OCOCH3), 0.80 (s, 3H, CH3).

−C NMR(CDCl3): δ178.54 (COOH), 171.78 (CH3COO), 82.83 (C3), 59.79 (CH2OH), 11.75 (C3a).

Elemental Analysis: For C20H32O5. Calcd: C, 68.15; H, 9.15; Found: C,68.01; H,9.27.

Structure:

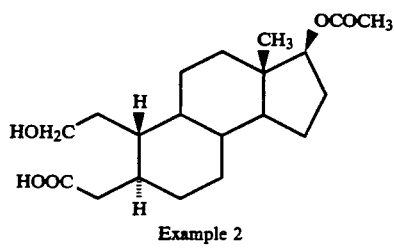

Example 2

EXAMPLE 3

Preparation of Methyl [3S-(3α,3aα,5aβ,6β, 7α,7aα, 9bβ)]-3-(Acetyloxy)dodecahydro-6-(2-hydroxyethyl)-3a-methyl-1-H-benz[e]indene-7-acetic acid To a solution of 3.52 g (10 mmol) of the compound of Example 2 in diethyl ether (350 mL), diazomethane in diethyl ether was added until a yellow color persisted at 0° C. The solution was allowed to stir for an additional 15 min. Excess diazomethane was destroyed by addition of several drops of formic acid. The mixture was washed with 10% aq. NaHCO$_3$(100 mL), water (100 mL), and brine (100 mL); and dried over Na$_2$SO$_4$. The solvent was removed to give a virtually quantitive yield of product, m.p. 72°73.5° C.

IR (film, NaCl): 3455, 2921, 2873, 1737, 1437, 1373, 1246 cm$^{-1}$.

$^1$H (NMR (CDCl$_3$): δ4.59 (t,J=7.7 Hz, 1H, CHOAc), 3.68 (s, 3H, COOCH$_3$), 3.68-3.61 (m, 1H, CH$_2$OH), 2.59 (dd, J=14.1 Hz, J=4.1 Hz, 1H of CH$_2$COOCH$_3$), 2.04 (s, 3H, OCOCH$_3$), 0.80 (s, 3H, CH$_3$).

$^{13}$C NMR(CDCl$_3$): δ174.47 (COOCH$_3$), 171.55 (CH$_3$COO), 82,75 (C$_3$), 60.02 (CH$_2$OH), 51.3 (CH$_3$O), 11.74 (C$_{3a}$).

Elemental Analysis: C$_{21}$H$_{34}$O$_5$. Calcd: C, 68.82.; H,9.35; Found: C,68.78; H,9.65

Structure:

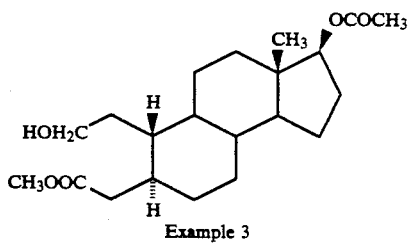

Example 3

EXAMPLE 4

Preparation of Methyl [3S-(3S-(3α, 3aα,3aα,5aβ, 6β,7α,9aα,9β)]-3-(Acetyloxy) dodecahydro-6-)2-oxoethyl)-3a-methyl-1H, benz[e]indene-7-acetic acid To a stirring suspension of pyridinium chlorochromatic (0.65 g, 3.0 mmol) and anhydrous NaOAc (0.25 g, 3.0 mmol) in dry dichloromethane (50 mL) was added a solution of the compound of Example 3 (0.73 g 2.0 mmol) in dry dichloromethane (10 mL) at room temperature under nitrogen. After the mixture was stirred for 2 h, diethyl ether (40 mL) was added. The mixture was filtered with A Bushier filter which was filled with silica gel and washed with cichloromethane. The solvent was removed to get a solid which was recrystalliced from diethyl ether to give 0.70 g (96.7%) pure product as colorless crystalline needles, m.p. 105°-170° C.

EXAMPLE 4

Preparation of

Methyl [3S-(3α,3aα,5aβ, 6β,7α,9aα,9bβ)]-3-(Acetyloxy)dodecahydro-6-(2-oxoethyl)-3a-methyl-1H-benz[e]indene-7-acetic acid To a string suspension of pyridinium chlorochromatic (0.65 g, 3.0 mmol) and anhydrous NaOAc (0.25 g, 3.0 mmol) in dry dichloromethane (50 mL) was added a solution of the compound of Example 3 (0.73 g 2.0 mmol) in dry dichloromethane (10 mL) at room temperature under nitrogen. After the mixture was stirred for 2 h, diethyl ether (40 mL) was added. The mixture was filtered with a Bushier filter which was filled with silica gel and whased wutg dichloromethane. The solvent was removed to get a solid which was recrystallized from diethyl ether to give 0.70 g (96.7&) pure product as colorless crystalline needles, m.p. 105°-107° C.

IR (film, NaCl) 2923, 2854, 2721, 1737, 1734, 1437, 1374, 1246 cm$^{-1}$.

$^1$H NMR (CDCl$_3$): δ9.82 (t, J=1.6 Hz, 1H, CHO), 4.59 (t, J=8.0 Hz, 1H, CHOAc), 3.67 (s, 3H, COOCH$_3$), 2.04 (s, 3, OCOCH$_3$), 0.80 (s, 3H, CH$_3$).

$^{13}$C NMR(CDCl$_3$): δ202.48 (CHO), 173.60 (COOCH$_3$), 171.40 (CH$_3$COO), 82.53 (C$_3$), 11.69 (C$_{3a}$).

Elemental Analysis: For C$_{21}$H$_{32}$O$_5$. Calcd: C, 69.29; H, 8.85; Found: C, 69.05, H, 8.78.

Structure:

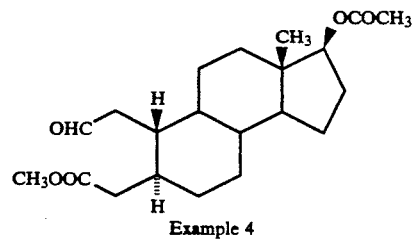

Example 4

EXAMPLE 5

Preparation of Methyl [3S-(3α,3aα,5aβ,6β,7α,9aα,9bβ)]-3-(Acetyloxy)-6-[2E-(acetyloxy)ethenyl]-dodecahydro-3a-methyl-1H-benz[e]indene-7acetic acid A solution of the compound of Example 4 (20 g, 55 mmol) and p-tolulenesulfonic acid (1.0 g, 5% w/w) in isopropenyl acetate (500 mL) was gently distilled for 2.0 h and about 25 mL of solution was collected. After refluxing for 14 h, the mixture was gently distilled for another 2.0 h and about 25 mL of solution gain was collected. The reaction mixture was cooled to room temperature and poured into dichloromethane (500 mL), and washed with water (100 mL) satd aq. NaHCO$_3$ 100 mL), and water (100 mL). The organic layer was dried over Na$_2$SO$_4$, filtered, and concentrated to give a yellow oil, which was chromatographed (silica gel, eluting with 4:1-hexane:ethyl acetate) to give 14 g (62%) pure product as colorless crystals, m.p. 122°-123° C.

IR (film NaCl): 2920, 1750, 1738, 1737, 1673, 1436, 1372, 1226 cm$^{-1}$.

$^1$H NMR (CDCl$_3$): δ7.01 (d, J=1.25 Hz, 1H, AcOCH=CH), 5.01 (dd, J=12.5 Hz, J=10.7 Hz, 1H, AcOCH=CH), 4.59 (t, J=7.8 Hz, 1H, CHOAc), 3.63 (s, 3H, COOCH$_3$), 2.49 (dd, J=15.4 Hz, J=4.4 Hz, 1H, of CH$_2$COOCH$_3$), 2.04 (s, 3H OCOCH$_3$), 0.79 (s, 3H, CH$_3$).

$^{13}$C NMR(CDCl$_3$): δ174.09 (OCH=), (=CH), 82.67 (CH$_3$COOCH=), 136.35 (OCH=), 117.35 (=CH), 82.67 (C$_3$), 11.80 (C$_{3a}$).

Elemental Analysis: For C$_{23}$H$_{34}$ O$_6$. Calcd: C, 67.96; H, 8.43. Found: C, 68.24; H, 8.53.

Structure:

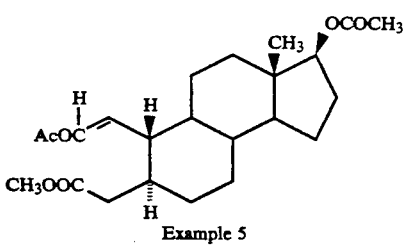

Example 5

EXAMPLE 6

Preparation of Methyl [3S-(3α,3aα,5aβ,6β,7α,9aα,9bβ)]-3-(Acetyloxy)-6-formyldodecahydro-3a-methyl-1H-benz[e]indene-7-acetic acid A solution of the compound of Example 5 (0.81 g, 2.0 mmol) in dichloromethane (50 mL) and acetic acid (0.5 mL) was cooled at 31 78° C. in an acetone—dry ice bath and treated in $O_3$ until a blue color persisted. The excess $O_3$ was removed by bubbling $O_2$. Methyl sulfide (4 drops, ca. 4.0 mmol) was added and the mixture was stirred for 1.0 h at 31 78° C. and 1.0 h at the room temperature. The mixture was diluted with dichloromethane (50 mL) and the organic layer was washed with water (50 mL), satd.aq. $NaHCO_3$ (50 mL), water (2×50 mL) again; and dried over $Na_2SO_4$. The organic solvent was removed to give a solid, which was recrystallized from diethyl ether to give 0.64 g (92%) of product as colorless crystals, m.p. 123°-124° C.

IR (film, NaCl): 2924, 2870, 2805, 2707, 1735, 1721, 1436, 1372, 1244 cm$^1$.

$^1$H NMR (CDCl$_3$): δ9.44 (d, J=5.4 Hz, 1H, CHO), 4.62 (t, J=8.5 Hz, 1H, CHOAc), 3.66 (s, 3H, COOCH$_3$), 2.04 (s, 3H, OCOCH$_3$), 0.80 (s, 3H, CH$_3$).

$^{13}$C NMR(CDCl$_3$): δ205.44 (CHO), 172.88 (COOCH$_3$), 171.38 (C$_3$COO), 82.41 (C$_3$), 11.71 (C$_{3a}$).

Elemental Analysis: For C$_{20}$H$_{30}$O$_5$. Calcd: C, 68.55; H, 8.63; Found: C, 68.71; H, 8.81.

Structure:

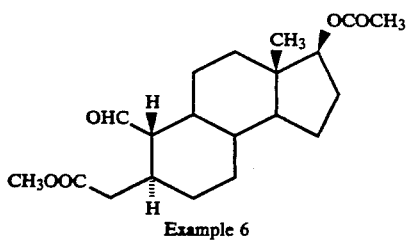

Example 6

EXAMPLE 7

Preparation of Methyl [3S-(3α,3aα,5aβ,7α,9aα,9bβ)]-3-(Acetyloxy)dodecahydro-3a-methyl-1H -benz[e]indene-7-acetic acid The mixture of the compound of Example 6 (0.70 g, 2.0 mmol) and Wilkinson's catalyst (1.85 g, 2.0 mmol) in benzonitrile (30 mL) was heated to 160° C. for 20 h under nitrogen. Most of the benzonitrile was removed by distillation and a mixture of ethyl acetate and hexane (1:1 v/v, 50 mL) was added to precipitate the organometallic by-product. The yellow solid was filtered and the solid was washed with cold ethyl acetate (2×20 mL). The combined organic layer was evaporated to give a viscous liquid, which was chromatographed (silica gel, 1% acetonitrile in dichloromethane) to give 0.59 g (91%) pure product as slightly yellow crystals, m.p. 62°-62° C.

IR (film, NaCl): 2918, 2851, 1741, 1738, 1446, 1373, 1246 cm$^{-1}$.

$^1$H NMR (CDCl$_3$): δ4.61 (t, J=8.5 Hz, 1H, CHOAc), 3.67 (s, 3H, COOCH$_3$), 2.04 (s, 3H, OCOCH$_3$), 0.80 (s, 3H, CH$_3$).

$^{13}$C NMR(CDCl$_3$): δ173.74 (COOCH$_3$), 171,44 (CH$_3$COO), 82.72 (C$_3$), 11.85. (C$_{3a}$).

Elemental Analysis: For C$_{19}$H$_{30}$O$_4$. Calcd: C, 70.77; H, 9.38; Found C, 70.68; H, 9.33.

Structure:

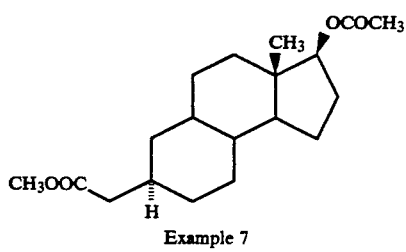

Example 7

EXAMPLE 8

Preparation of [3S-(3α,3aα,5aβ,7α,9aα,9bβ)]-Dodecahydro-3-hydroxy-3a-methyl-1H-benz[e]indene-7-acetic acid To a solution of the compound of Example 7 (100 mg, 0.38 mmol) in methanol (10 mL) was added an aq. solution of NaOH (0.19 g in 2 mL water). After stirring at room temperature for 18 h, aq. HCl (6N, 20 mL) was added and the reactio mixture was poured into water (100 mL). The product precipitated and was recovered as a white solid by filtration. It was recrystallized from aq. methanol to give 67 mg (81% yield) pure proudct as fine white crystals, m.p. 202°-203° C.

IR (film, AgCl): 3401, 2895, 1703, 1338, 1233, 1056 cm$^{-1}$.

$^1$H NMR (CDCl$_3$): δ3.66 (t, J=8.3 Hz, 1H, CHOH),a 2.24 (d, J=6.8 Hz, 1H of CH$_2$COOH), 0.75 (s, 3H, CH$_3$),

Elemental Analysis: For C$_{16}$H$_{26}$O$_3$. Cacd: C, 72.14; H, 9.84; Found: C, 71.91; H, 9.62.

Structure:

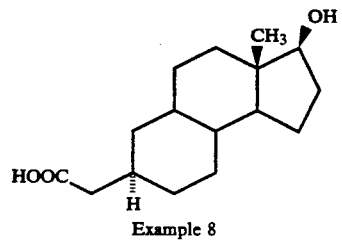

Example 8

EXAMPLE 9

Preparation of
[3S-(3α,3aα,5aβ,7α,9aα,9bβ)]-Dodecahydro-3-hydroxy-3-a-methyl-1H- benz[indene-7-ethanol To a stirred, cooled (ice-water bath) solution of the compound of Example 7 (0.65 g, 2.0 mmol) in dry toluene (50 mL) was added diisobutyl aluminium hydride (1.0 M solution in toluene, 12 mL, 12 mmol). After 3.0 h, toluene-methanol (1:1, 4 mL) was added and followed by 10% aw. HCl (10 mL). Then the mixture was washed with water 2×50 mL) and brine (50 mL). The organic layer was dried over $Na_2SO_4$, filtered and concentrated under reduced pressure to give a solid, which was recrystallized from ethyl alcohol to yield 0.47 g (93%) of pure product as colorless crystals, m.p. 145°-147° 61 C.

IR (film, NaCl): 3279, 2914, 2870, 2858, 2841, 1469, 1443, 1381, 1348, 1067, 1056 cm$^{-1}$.

$^1$H NMR (CDCl$_3$): δ3.73-3.65 (m, 3H, CH$_2$OH and CHOH), 0.76 (s, 3H, CH$_3$).

$^{13}$C NMR (CD$_3$OD): δ82.63 (C$_3$), 60.78 (CH$_2$OH), 11.71 C$_{3a}$).

Elemental Analysis: for $C_{16}H_{28}O_2$. Cacd: C, 76.14; H, 11.18; Found: C, 75.96; H, 11.29

Structure:

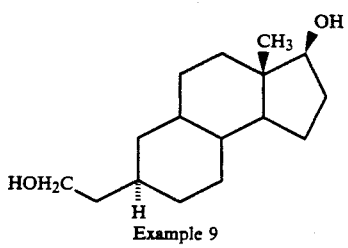
Example 9

EXAMPLE 10

Preparation of
[3aS-(3aα,5aβ,7α,9aα,9bβ)]-7-(2-Hydroxyethyl)-dodecahydro-3a-methyl-3H -benz[e]inden-3-one To a stirred solution of the compound of Example 9 (254 mg, 1.0 mmol) in glacial acetic acid (5 mL) was added dropwise a 5.25% solution of sodium hypochlorite (1.5 mL, 1.05 mmol) at room temperature over 10 min. After the stirring was continued for another 1.0 h, isopropanol (2.0 mL) was added to quench any excess oxidant, followed by water (5.0 mL). The mixture was extracted with ethyl acetate (2×25 mL). The combined organic layer was washed with water (25 mL), satd. aq NaHCO$_3$(25 mL), water (25 mL), and brine; (25 mL) and dried over Na$_2$SO$_4$. The solvent was removed to give an oil, which was purifief by column chromatography (silica gel, eluted with 1:1 ethyl acetate-hexane) to give 161 mg (64%) of pure product as colorless crystals (from diethyl ether-hexane), m.p. 38°-40° C.

IR (film, NaCl): 3435, 2917, 1739, 1452, 1406, 1373, 1258, 1097, 1046, cm$^{-1}$.

$^1$H NMR (CDCl$_3$): δ3.71 (t, J=6.5 Hz, 2H, CH$_2$OH), 0.87 (s, 3H, CH$_3$). $^{13}$C NMR(CDCl$_3$): δ222.05 (CO), 60.07 (CH$_2$OH), 13.44 (C$_{3a}$).

Elemental Analysis: For $C_{16}H_{26}O_2$. Calcd: 76.75; H, 10.47; Found; C, 76.52; H, 10.24

Structure:

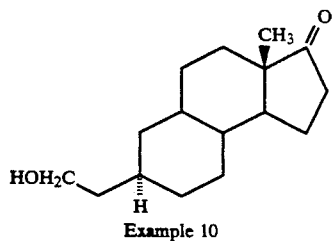
Example 10

EXAMPLE 11

Preparation of
[3S-(3α,3aα,5aβ,7α,9aα,9bβ)]-7-(2-Hydroxyethyl)-dodecahydro-3a-methyl-1H-benz[e]indene-3-cyclopropylamine To a solution of anhydrous cyclopropylamine (170 mg, 3.0 mmol) in absolute methanol (10 mL) was added a solution of the compound of Example 10 (10 mg, 0.6 mmol) in methanol (5.0 61 mL) and then NaBH$_3$CN (62 mg, 1.0 mmol) at room temperature under nitrogen. The pH value of the mixture was adjusted to equal about 6 with methanolic HCl solution. After the mixture was stirred for 72 h at room temperature, the solvent was evaporated under vacuum and the residue was dissolved in 6 N aq.HCl and extracted with diethyl ether (3×25 mL). The solution was made basic with satd. NaOH solution and was saturated with NaCl. The free amine crystallized on the surface of the solution and was extracted with diethyl ether (33×50 mL). The combined solutions were evaporated. The residue was dissolved in methanol (10 mL) and bubbled with HCl gas until strongly acidic. Most of the methanol was removed under vacuum to give a residue which was recrystallized from methanol-ethyl acetate-hexane to give 120 mg (61%) of pure product as colorless crystalline needles, m.p. 220°-222° C.

IR (KBr): 3400, 3379, 3051, 2918, 2845, 2795, 2732, 1591, 1446, 1052, 1036 cm$^{-1}$.

$^1$H NMR (CD$_3$OD) δ3.52 (t, J=6.5 Hz, 2H CH$_2$OH), 0.83 (s, 3H, CH$_3$).

$^{13}$C NMR(CD$_3$OD): δ70.39 (C$_3$), 60.70 (CH$_2$OH), 12.28 (C$_{3a}$).

Elemental Analysis: For $C_{19}H_{34}ClNO$. Calcd: C, 69.59; H, 10.45; N, 4.27; Cl, 10.81. Found: C, 69.46; H, 10.47; N, 4.24; Cl, 11.00.

Structure:

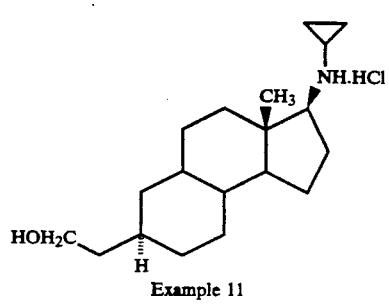
Example 11

EXAMPLE 12

Preparation of
[3S-(3α,3aα,5aβ,7α,9aα,9bβ)]-7-(2-Hydroxyethyl)-
dodecahydro-3a-methyl
-1H-benz[e]indene-3-carbonitrile A solution of the compound of Example 10 (320 mg 1.28 mmol) in dimethoxyethane (32 mL) was treated with a 1.0 M solution of t-BuOK in dimethyoxyethane (12.8 mL, 12.8 mmol) and ethanol (2.0 mL). A solution of tosylmethyl isocyanide (500 mg, 2.56 mmol) in dimethoxyethane (6.5 mL) was added very slowly by means of a syringe over 20 min with stirring at room temperature. After 3.0 h, the mixture was quenched with water (50 mL) and extracted with ethyl acetate (3×50 mL). The organic layers were combined and washed with water (2×50 mL) and bringe (50 mL); and dried over $Na_2SO_4$. The solvent was removed to get an oil, which was purified by chromatography (silica gel, eluted with 10% acetonitrile in dichloromethane) to give 200 mg (60%) of a mixture of 17α- and 17β-nitrile isomers as a colorless oil. $^{13}C$ NMR spectra of this mixture showed two peaks δ 122.22 and δ 121.27 respectively, and their ratio was 38:62. The isomers were separated by HPLC (Ultrasphere-Si, 5 μ, 250 mm×10 mm column eluted with 30% ethyl acetate in hexane at 3.0 mL/min) to give 90 mg (27%) of pure product (β isomer), which was recrystallized from diethyl ether and hexane as colorless crystals, m.p. 82°-83° C.

IR (Film, NaCl): 3294, 2917, 2853, 2233, 1470, 1384, 1338, 1056, 1021 $cm^{-1}$.

$^1H$ NMR ($CDCl_3$): δ 3.64–3.61 (m, 2H, $CH_2OH$), 0.88 (s, 3H, $CH_3$).

$^{13}C$ NMR ($CDCl_3$): δ 121.43 (CN), 60.30 ($CH_2OH$), 14.06 ($C_{3a}$).

Elemental Analysis: For $C_{17}H_{27}NO$. Calcd: C, 78.11; H, 10.51; N, 5.36; Found: C, 78.38; H, 10.26; N, 5.28.

Structure:

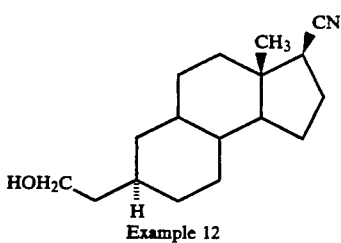
Example 12

EXAMPLE 13

Preparation of
[3S-(3α,3aα,5aβ,7α,9aα,9bβ)]-1-[7-(2-Hydroxyethyl)-
dodecahydro-3a-methyl-1H-bene[e]inden-3-yl-etha-
none To a solution of methylmagnesium iodide (3.0 M solution is diethyl ether, 1.7 mL, 5.0 mmol) was added a solution of the compound of Example 12 (260 mg, 1.0 mmol) in dry tetrahydrofuran (10 mL) at ice-water bath temperature under nitrogen. Then the mixture was refluxed for 24 h. After the reaction was cooled down to 0° C., satd. aq. $NH_4Cl$ solution was added to destroy any excess Grignard reagent. The mixture was extracted with ethyl acetate (3×25 mL). The combined organic layer was dried over $Na_2SO_4$ and evaporated to give an oil, which was purified by chromatography (10% acetonitrile in dichloromethane) to give 249 mg (90%) of pure product as colorless crystals (from ethyl ether and hexane), m.p. 61°-62° C.

IR (Film, NaCl): 3391, 2916, 1705, 1447, 1384, 1056 $cm^{-1}$.

$^1H$ NMR ($CDCl_3$) δ 3.69 (t, J=6.6 Hz, 2H, $CH_2OH$), 2.12 (s, 3H, $COCH_3$), 0.62 (s, 3H, $CH_3$).

$^{13}C$ NMR($CDCl_3$): δ 210.34 (CO, 60.54 ($CH_2OH$), 13.22 ($C_{3a}$).

Elemental Analysis: For $C_{18}H_{30}O_2$. Calcd: C, 77.65; H, 10.86; Found: C, 77.68; H, 10.83.

Structure:

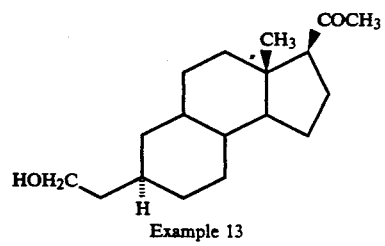
Example 13

EXAMPLE 14

Preparation of
[3S-(3α,3aα,5aβ,6β,7α9aα,9bβ)]-3-(acetyloxy)-
dodecahydro-6-(2)
hydroxyethyl)-3a,6-dimethyl-1H-benz[e]indene-7-
acetic acid A solution of an approximately 8:2 mixture of 3,17β-diacetoxyandrost-3-ene and 3,17β-diacetoxyandrost-2-ene 9.7 g, 26.9 mmol) in dichloromethane (400 mL) and acetic acid (30 mL) was treated with $O_3$ at −78° C. until a blue color persisted. Excess $O_3$ was discharged by an $O_2$ stream until colorless and then the addition of methyl sulfide (1 drop). The dichloromethane was removed on a rotary evaporator, and water (90 mL) and acetic acid (200 mL) was added to the remaining solution. After stirring overnight to hydrolyze the anhydride group generated during ozonolysis, water (200 mL) and diethyl ether (200 mL) were added. The diethyl ether layer was repeatedly washed with water to remove acetic acid and then dried over $MgSO_4$. Solvent removal yielded a slightly yellow solid (10.7 g) that dissolved in methanol (200 mL) cooled to 0° C., and reacted with slowly added portion of $NaBH_4$ (14.3 g). Fifteen min after $NaBH_4$ addition was completed, 10% aq. HCl was added until the solution became acidic. Water (250 mL) was added, and methanol removal on a rotary evaporator was accompanied by the precipitation of the steroid product. After filtration and air drying the crude product (8.2 g, 87%) was obtained as a white solid. Recrystallization from methanol yielded the pure product which hand m.p. 182°-184.5° C.

IR (film, AgCl) 3319, 1247, 1214, 1729, 1692 $cm^{-1}$.

$^1H$ NMR ($CDCl_3$) δ 4.58 (t, J=10.8 Hz, 1H, CHOAc), 3.72 (m, 2H, $CH_2OH$), 2.62 (d, J=12.9 Hz, 1H of $CH_2COOH$), 2.04 (s, 3H, $OCOCH_3$), 0.77 (s, 6H, $CH_3$($C_{3a}$) and $CH_3$ ($C_6$)).

Elemental Analysis: For $C_{21}H_{34}O_5$. Calcd: C, 68.92; H, 9.35. Found: C, 69.29; H, 9.29.

Structure:

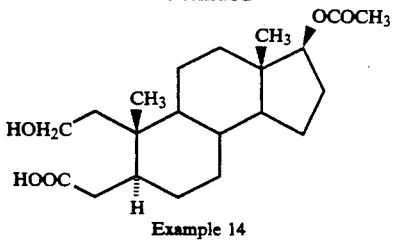

Example 14

EXAMPLE 15

Preparation of Methyl
[3S-(3α,3aα,5aβ,6β,7α,9aα,9bβ)]-3-(Acetyloxy)-dodecahydro-6-(2-hydroxyethyl)-3a,6-dimethyl-1H-benz[e]indene-7-acetic acid To a solution of 5.4 g (17.8 mmol) of the compound of Example 14 in diethyl ether (150 mL), diazomethane in diethyl ether was added until a yellow color persisted. The solution was allowed to stir for an additional 15 min. Excess diazomethane was destroyed by addition of several drops of formic acid. The solvent was removed on a rotary evaporator and the crude product was purified by chromatography (silica gel eluted with 40% ethyl acetate in hexane). The purified product (4.7 g, 83%) was obtained as a solid which after recrystallization from a mixture of diethyl and hexane had m.p. 115.5°–117.5° C.

IR (film, AgCl) 3453, 2934, 1732, 1438, 1373, 1246 cm$^{-1}$.

$^1$H NMR (CDCl$_3$) δ 4.58 (t, 1H, J=8.5 Hz, CHOAc), 3.73 (m, 1H of CH$_2$OH), 3.68 (s, 3H, COOCH$_3$), 3.63 (m, 1H of CH$_2$OH), 2.56 (dd, J=14.4 Hz, 2.4 Hz, 1H of CH$_2$COOCH$_3$), 2.04 (s, 3H, OCOCH$_3$), 0.77 (s, 6H, CH$_3$ (C$_{3a}$) and CH$_3$ (C$_6$)).

Elemental Analysis: For C$_{22}$H$_{36}$O$_5$. Calcd: C, 69.44; H, 9.54. Found: C, 69.23; H, 9.52.

Structure:

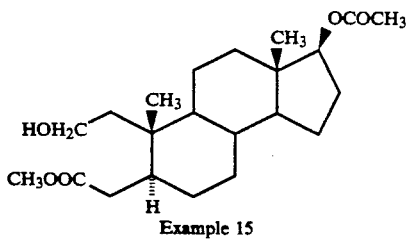

Example 15

EXAMPLE 16

Preparation of Methyl
[3S-(3α,3aα,5aβ,6β,7α,9aα,9bβ)]-3-(Acetyloxy)-6-[2E-(acetyloxy)ethenyl]-dodecahydro-3a,6-dimethyl-1H-benz[e]indene-7-acetic acid and Methyl
[3S-(3α,3aα,5aβ,6β,7α,9aα,9bβ)]-3-(Acetyloxy)-6-[2Z-(acetyloxy)ethenyl]-dodecahydro-3a,6-dimethyl-1H-benz[e]indene-7-acetic acid A solution of the compound of Example 15 (4.7 g, 12.3 mmol) in dichloromethane (50 mL) was added rapidly to a suspension of pyridinium chloroformate (10.81 g, 50.15 mmole) in dichloromethane and stirred at room temperature under nitrogen. After 3 h, the volume of dichloromethane was reduced to 40 mL on a rotary evaporator and then poured into diethyl ether (750 mL). The ether was passed through a small column of Florisil and additional diethyl ether was used to wash the Florisil and elute the steroid. The diethyl ether was removed on a rotary evaporator and the crude aldehyde product (4.6 g) immediately combined with isopropenyl acetate (60 mL) and p-toluenesulfonic acid (0.5 g) and reflexed for 16 h. The solution was then gently distilled for 1 h until about 10 mL of distillate was collected and then cooled to a room temperature. The solution was poured into dichloromethane and washed with water (50 mL), 5% aq. NaHCO$_3$, and water (3×100 mL). The organic layer was dried over MgSO$_4$, filtered, and removed on a rotary evaporator to give slightly yellow crystals (5.6 g), which were purified by chromatography (silica gel eluted with 4% ethyl acetate in dichloromethane) to give 3.7 g of product. Recrystallization from a mixture of ethyl acetate and hexane gave 1.83 g (36%) of a mixture of the E and Z enol acetates. The enol acetate isomers were separated by high performance liquid chromatography (Econosil 5 micron, 250 mm×4.6 mm, eluted at 2.0 mL/min with 10% ethyl acetate in hexane).

EXAMPLE 16 CONTINUED

The major 6-[2E-(acetyloxy)ethenyl] isomer had m.p. 191°–192° C.

IR (film, AgCl): 2918, 1756, 1733, 1666, 1451, 1373, 1227 cm$^{-1}$.

$^1$H NMR (CDCl$_3$): δ 6.98 (d, J=12.7 Hz, 1H, AcOCH=CH), 5.15 (d, J=12.7 Hz, 1H, AcOCH=CH), 4.56 (t, J=8.5 Hz, 1H, CHOAc), 3.63 (s, 3H, COOCH$_3$), 2.41 (dd, J=15.2 Hz, J=2.8 Hz, 1H of CH$_2$COOCH$_3$), 2.03 (s, 3H, OCOCH$_3$), 2.11 (s, 3H, OCOCH$_3$), 0.87 (s, 3H, CH$_3$ (C$_6$)), 0.76 (s, 3H, CH$_3$ C$_{3a}$)).

Elemental Analysis: For C$_{24}$H$_{36}$O$_6$. Calcd: C, 68.55; H, 8.63. Found: C, 68.75; H, 8.70

Structure:

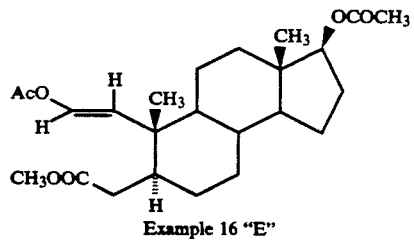

Example 16 "E"

The minor 6-[2Z-(acetyloxy)ethenyl] isomer had m.p. 109.5°–112° C.

IR (film, AgCl): 2936, 1759, 1735, 1668, 1437, 1371, 1246, 1217 cm$^{-1}$.

$^1$H NMR (CDCl$_3$): δ 6.70 (d, J=7.6 Hz, 1H, AcOCH=CH), 4.58 (t, J=8.5 Hz, 1H, CHOAc), 4.39 (d, J=7.5 Hz, 1H, AcOCH=CH), 3.64 (s, 3H, COOCH$_3$), 2.44 (d, J=14.3 Hz, 1H of CH$_2$COOCH$_3$) 2.11 (s, 3H, OCOCH$_3$), 2.03 (s, 3H, OCOCH$_3$), 1.06 (s, 3H, CH$_3$(C$_6$)), 0.79 (s, 3H, CH$_3$ (C$_{3a}$)).

Elemental Analysis: For C$_{24}$H$_{36}$O$_6$. Calcd: C, 68.55; H, 8.63. Found: C, 68.93; H, 8.73.

Structure:

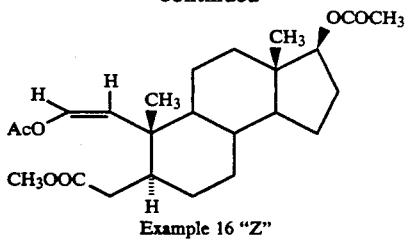

Example 16 "Z"

EXAMPLE 17

Preparation of [Methyl [3S-(3α,3aα,5aβ,6α,7α,9bβ)]-3-(Acetyloxy)dodecahydro-3a, 6-dimethyl-1H-benz[e]indene-7-acetic acid A solution of a mixture of the enol acetates of Example 16 (200 mg, 0.48 mmol) in dichloromethane (25 mL) and acetic acid (0.5 mL) was cooled to −78° C. in an acetone—dry ice bath and treated with $O_3$ until a blue color persisted. The excess $O_3$ was removed by bubbling the solution with $O_3$. After adding methyl sulfide (1 drop), dichloromethane (75 mL) was added and the solution was washed with water, 5% aq. $NaHCO_3$, and water again, The dichloromethane was drived over $NgSO_4$, filtered, and removed on a rotary evaporator to yield a yellow aoil (158 mg). The oil was combined with Wilkinson's catalyst (3×500 mg added in equal portions, initially and after 72 and 120 h) in benzonitrile (25 mL) and heated to 150°-180° C. for 144 h under nitrogen. After cooling, ethyl acetate (50 mL) was added and the mixture was filtered. Removal of the solvents from the filtrate yielded a brown sludge (2.0 g) which was chromatographed (silica gel eluted with hexane/ethyl acetate mixtures) to give 25.4 mg (17.5%) pure produce as a white solid, m.p. 61°-63° C.

IR(film, AgCl): 2922, 1737, 1437, 1373, 1248 cm$^{-1}$.

$^1$H NMR (CDCl$_3$): δ 4.61 (t, J=7.82 Hz, 1H, CHOAc), 3.67 (s, 3H, COOCH$_3$), 2.56 (s, 3H, OCOCH$_3$), 0.78 (s, 3H, CH$_3$), 0.77 (s, 3H, CH$_3$).

Elemental Analysis: For C$_{20}$H$_{32}$O$_4$. Calcd: C, 71.39; H, 9.59; Found: C, 70.96; H, 9.62.

Structure:

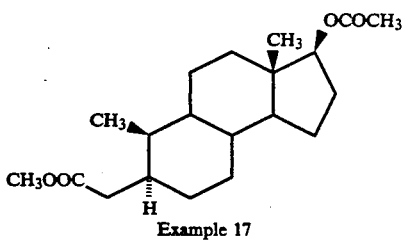

Example 17

EXAMPLE 18

Preparation of [3S-(3α,3aα,5aβ,6α,7α,9aα,9bβ)]-Dodecahydro-3a,6-dimethyl-1H-benz[e]indene-7-acetic acid To a solution of the compound of Example 17 (674 mg, 2.0 mmol) in methanol (50 mL) was added an aq. solution of NaOH (0.38 g in 5 mL water). After stirring at room temperature for 18 h, aq. HCl (6N, 20 mL) was added, and the reaction mixture was puored into water (10 mL). The produce precipiated and was recovered as a white solid by filtration. It was recrystallized from aq. methanol to give 418 mg (74%) pure product as fine white crystals, m.p. 208°-210° C.

IR (film, NaCl): 3367, 2926, 1710, 1352, 1055, 1032 cm$^{-1}$.

$^1$H NMR (CDCl$_3$); δ 3.62 (t, J=8.8 Hz, 1H, CHOH), 0.76 (d, J=6.1 Hz, 3H, CH$_3$ (C$_6$)), 0.71 (s, 3H, CH$_3$(C$_{3a}$)).

Elemental Analysis: For C$_{17}$H$_{28}$O$_3$. Calcd: C, 72.82; H, 10.06; Found: C, 73.00; H, 10.18.

Structure:

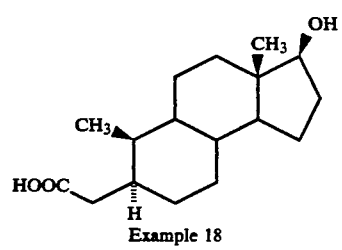

Example 18

EXAMPLE 19

Hippocampal Cell Culture methods

Under halothane anesthesia, 1 day old albino rat pups are sacrificed by rapid decapitation and the hippocampi are dissected and dissociated with papain (1 mg/ml in oxygenated L-15 media for 30 min at 35° C.) and mechanical trituration (18). Cells are plated on collagen coated-culture dishes at a density of 300,000 cells/ml. The growth media consists of Eagles Minimal Essential Media (MEM) supplemented with 5% fetal calf serum, 5% horse serum, 17 mM glucose, 0.4 mM glutamine, 50 U/ml penicillin and 50 μg/ml streptomycin. After three days in culture cells are treated with 10 μM cytosine arabinoside (ARA-C) to suppress glial growth. Cells are subsequently fed with fresh media once per week.

Electrophysiological Methods

For recording purposes the growth media is replaced with a solution containing (in mM): 140 NaCl, 5 KCl, 2 CaCl$_2$, 1 MgCl$_2$, 10 glucose, 10 HEPES, 0.001 tetrodotoxin, pH=7.3. Neurons are studied using patch clamp recording techniques (12) with pipettes containing (in mM): 145 CsCl, 5 BAPTA, 5 NaCl, 0.5 CaCl$_2$, 2 MgATP, 10 HEPES, pH=7.3. This CsCl intracellular solution sets the Cl$^{-1}$ equilibrium potential (E$_{cl}$) at 0 mV (i.e. symmetric transmembrane concentrations of Cl$^-$). This allows reliable recording of Cl$^{-1}$ currents without concern for shifts in transmembrane Cl$^{-1}$ concentration which can alter GABA responses during longer agonist exposures (1). In some tests examining effects on GABA IV curves, E$_{cl}$ is manipulated by replacing CsCl with CsMeSO$_4$. This shifts E$_{cl}$ to −81 mV. By comparing changes in IV curves in the two intracellular solutions greater confidence is had that responses are mediated by Cl$^-$-selective ion channels. BAPTA and MgATP are included in the recording pipette to prevent problems with response rundown which sometimes occurs in whole-cell recording (44). The tests are conducted at room temperature (22° C.).

Table 1, below, sets forth the results obtained in the potential of GABA currents with the four illustrative preferred tricyclic steroid compounds compared to the control compound, 3α-OH-DHP.

TABLE 1

Potentiation of GABA Currents by Tricyclic Analogs

| Compound | Concentrations Tested 0.1 μM (N) | 1.0 μM (N) | Concentration for Direct Cl⁻ Current Activation |
|---|---|---|---|
| [Steroid structure: 3α-hydroxy-5α-pregnan-20-one] | 110 ± 5(3) | 195 ± 16(9) | >1 μM |
| [Tricyclic analog] R = =O | 95 ± 3(6) | 127 ± 5(6) | * |
| R = CN | 176 ± 9(8) | 346 ± 2(6) | * |
| R = NH—△ (cyclopropylamino) | 237 ± 18(7) | 433 ± 20(8) | * |
| R = COCH₃ | 297 ± 7(11) | 489 ± 19(12) | * |

*No response up to 10 μM.
Values represent mean ± SEM; results are expressed as percent of control response to 1 μM GABA.

Various other examples will be apparent to the person skilled in the art after reading the present disclosure without departing from the spirit and scope of the invention. It is intended that all such other examples be included within the scope of the appended claims.

LITERATURE CITED

1. Akaike N, Inomata N, Tokutomi N (1987). Contribution of chloride shifts to the fade of γ-aminobutyric acid-gated currents in frog dorsal root ganglion cells. *J. Phyisol*, (London) 391, 219-234.
2. Baker K, Yang J, Covey D F, Clifford D B, Zorumski C F (1988). Alpha substituted thiobutyrolactones potentiate GABA currents in voltage clamped chick spinal cord neurons. *Neurosci. Lett.*, 87, 133-138.
3. Barker J L, Harrison N L, Lange, G D, Owen D G (1987). Potentiation of gamma-aminobutyric-acid-activated chloride conductance by a steroid anaesthetic in cultured rat spinal neurones. *J. Physiol.* (London), 386, 485-501.
4. Baulieu E E, Robel P (1990). Neurosteroids: a new brain function? *J. Steroid Biochem. Molec. Biol.*, 37, 395-403.
5. Borman J (1988). Electrophysiology of GABA$_A$ and GABA$_B$ receptor subtypes. *Trends Neurosci.*, 11, 112-116.
6. Callachan H, Cottrell G A, Hather N Y, Lamber J J, Nooney J M, Peters J A (1987). Modulation of the GABA$_A$ receptor by progesterone metabolies. *Proc. R. Soc. Lond. B*, 231, 359-369.
7. Choi D W, Farb D H, Fischbach G C (1981). Chlordiazepoxide selectively potentiates GABA conductance of spinal cored and sensory neurons in cell culture. *J. Neurophysiol*, 45, 621-631.
8. Crawley, J N, Glowa J R, Majewska M D, Paul S M (1986). Anxiolytic activity of an endogenous adrenal steroid. *Brain Research*, 398, 382-385.
9. Dryden, Jr. H L, (1972). Reductions of steroids by metal-ammonia solutions. In: *Organic Reactions in Steroid Chemistry*. (Eds. Fried J and Edwards J A) Van Nostrand Reinhol, New York, pp. 1-60.
10. Gee K W (1988). Steroid modulation of the GABA/benzodiazepine receptor-linked chloride ionophore. *Mol. Neurobiol.*, 2, 291-317.
11. Gee K W, Bolger M B., Brinton R E, Coirini, McEwens B S (1988). Steroid modulation of the chloride ionophore in rat brain: structure-activity requirements, regional dependence and mechanism of action. *J. Pharmaciol. Exp. Ther.*, 246, 803-812.
12. Hamill O P, Marty A, Neher E, Sakmann B, Sakmann F J (1981). Improved patch-clamp techniques for high resolution current recordings from cells and cell-free membrane patches. *Pfluegers Arch.* 391, 85-100.
13. Harrison, N L, Majewska M D, Harrington, J W, Barker J L (1987). Structure-activity relationships for steroid interaction with the gamma-aminobutyric acid$_A$ receptor complex. *J. Pharmacol. Exp. Ther.*, 241, 346-353.
14. Harrison, N L, Vicini S, Barker J L (1987). A steroid anesthetic prolongs inhibitory postsynaptic currents in cultured rat hippocampal neurons. *J. Neurosci.*, 7, 604-609.
15. Harrison, N L, Majewska, M D, Meyers D E R, Barker J L (1989). Rapid actions of steroids on CNS neurons. In: *Neural Control of Reproductive Function*. Alan Liss, New York, pp. 137-166.
16. Holland, K D, Ferrendelli, J A, Covey, D F, Rothman S M (1990). Physiological regulstions of the pictotoxin receptor by γ-butyrolactones in cultured hippocampal neurons. *J Neurosci.* 10, 1719-1727.
17. Holland K D, Yoon K W, Ferrendelli J A, Covey D F, Rothman S M (1991). γ-Butyrolactone antagonism of the picrotoxin receptor: comparison of a pure antagonist and a mixed antagonest/inverse agonist. *Mol. Pharmacol.* 39, 79-84.
18. Huettner J E, Baughman R W (1986). Primary culture of identified neurons from the visual cortex of postnatal rats. *J. Neurosci.* 8, 160-175.
19. Im W B, Blakeman D P, Davis J P, Ayer D E (1990). Studies on the mechanism of interactions between anesthetic steroids and γ-aminobutyric acid$_A$ receptors. *Mol. Pharmacol.* 37, 429-434.

20. Kavaliers M (1988). Inhibitory influences of the adrenal steroid, 3α,5α-tetrahydroxycorticosterone on aggression and defeat-induced analgesia in mice. *Psychopharmacology*, 95, 488–492.
21. Majewska M D (1988). Interaction of ethanol with the $GABA_A$ receptor in the rat brain: possible involvement of endogeneous steroids. *Alcohol*, 5, 269–273.
22. Majewska M D, Mienville J M, Vicini S (1988). Neurosteroid pregnenolone sulfate antagonizes electrophysiological responses to GABA in neurones. *Neuroscience Lett.*, 90, 279–284.
23. Majewska M D, Demirgoren S, Spivak C E, London E D (1990). The neurosteroid dehydroepiandrosterone sulfate is an allosteric antagonist of the $GABA_A$ receptor. *Brain Research*, 526, 143–146.
24. Majewska M D, Harrison N L, Schwartz R D, Barker J L, Paul S M 91986). Steroid hormone metabolites are barbiturate-like modulators of the GABA receptor. *Science*, 232, 1004–1007.
25. Majewska M D (1987). Steroids and brain activity. *Biochem. Pharmacol.*, 22, 3781–3788.
26. Mendelson W B, Martin J V, Perlis M, Wagner R, Majewska M D, Paul S M (1987)./ Sleep induction by an adrenal steroid in the rat. *Psychopharmacology*, 93, 226–229.
27. Mienville J M, Vicini S (1989). Pregnenolone sulfate antagonizes, $GABA_A$ receptor-mediated currents via a reduction of channel opening frequency. *Brain Res.* 489, 190–194.
28. Morgan M, Whitman J G (1985). Althesin. *Anesthesia*, 40, 121–123.
29. Morow A L, Pace J R, Purdy R H, Paul S M (1990). Characterization of steroid interactions with gamma-aminobutyric acid receptor-gated chloride ion channels: evidence for multiple steroid recognition sites. *Mol. Pharmacol.*, 37, 263–270.
30. Murphy B E P (1991). Steroids and depression. *J Steroid Biochem. Molec. Biol.* 38, 537–559.
31. Ong J, Kerr D I B, Johnston G A R (1987). cortisol: a potent biphasic modulator at $GABA_A$-receptor complexes in the guinea pig isolated lileum. *Neurosci. Lett.*, 82, 101–106.
32. Peters J A, Kirkness E F, Callahan H, Lambert J J, Turner A J (1988). Modulation of the $GABA_A$-receptor by depressant barbiturates and pregnane steroids. *Br. J. Pharmacol.*, 94, 1257–1269.
33. Peterson S L (1989). Anticonvulsant profile of an anesthetic steroid. *Neuropharmacology*, 28, 877–879.
34. Phillipps G H (1974). Structure-activity relationship in steroidal anesthetics. In: *Molecular Mechanisms In General Anaesthea*, (Eds. Halsey M J, Millar R A, Sutton J A), Churchill Livingstone, New York, pp. 32–46.
35. Puia G, Santi M-R, Vicini S, Pritchett D B, Purdy R H, Paul S M, Seeburg P h, costa E. (1990). Neurosteroids act on recombinant human $GABA_A$ receptors. *Neuron*, 4, 759–765.
36. Purdy R H, Morrow A L, Moore, Jr. P H, Paul S M (1991). Stress-induced elevations of gamma-aminobutyric acid type A receptor-active steroids in the rat brain. *Proc. Natl. Acad. Sci. USA*, 88, 4553–4557.
37. Purdy R H, Morrow A L, Blinn J R, Paul S M (1990). Synthesis, metabolism, and pharmacological activity of 3α-hydroxy steroids which potentiate GABA-receptor-mediated chloride ion uptake in rate cerebral cortical synaptoneurosomes. *J. Med. Chem.*, 33, 1572–1581.
38. Rosciszewska D, Buntner B, Guz I, Zawisza L (1986). Ovarian hormones, anticonvulsant drugs, and seizures during the menstrual cycle in women with epilepsy. *J. Neurol. Neurosurg. Psych.*, 49, 47–51.
39. Scholfield C N (1980). Potentiation of inhibition by general anesthetics in neurons of the olfactory cortex. *Pflugers Arch.*, 383, 249–255.
40. Schulz D W, MacDonald R L (1981). Barbiturate enhancement of GABA-mediated inhibittion and activation of chloride ion conductance: correlation with anticonvulsant and anesthetic actons. *Br. Res*, 209, 177–188.
41. Segal M, Barker J L (1984). Rat hippocampal neurons in culture: voltage clamp analysis of inhibitory connections. *J. Neurophysiol*, 52, 469–487.
42. Selye H (1941). Anesthetic effect of steroid hormones. *Proc. Soc. Exp. Biol. Med.*, 46, 116–121.
43. Sharpless K B, Lauer R F, Teranishi A Y (1973). Electrophilic and nucleophilic organoselenium reagents. New routes to α, β-unsaturated carbonyl compounds. *J. Amer. Chem. Soc.*, 95, 6137–6139.
44. Stelzer A, Kay A R, Wong R K S (1988). $GABA_A$ receptor function is hippocampal cells is maintained by phosphorylation factors. *Science* 241, 339–341.
45. Stude R D, Barker J L (1981). Diazepam and (−)pentobarbital: fluctuation analysis reveals different mechanism for potentiation of GABA responses in cultured central neurons. *Proc. Natl. Acad. Sci. (USA)* 78, 7180–7184.
46. Tsuji N, Suzuki J, Shiota M, Takahaski I, Nishimura S (1980). Highly stereoselective hydrogenation of 3-oxo-4-ene and 1,4-diene steroids to 5β compounds with palladium catalyst. *J. Org. Chem.*, 45, 2729–2731.
47. Turner D M, Ransom R W, Yang JS-J, Olsen R (1989). Steroid anesthetic and naturally occurring analogs modulate the gamma-Aminobutyric acid receptor complex at a site distinct from barbiturates. *J. Org. Chem.*, 45, 2729–2731.
48. Zorumski C F, Yang J, Baker K, Covey D F, Clifford D B (1989). Convulsant gamma-butyrolactones block GABA currents in cultured chick spinal cored neurons. *Brain Res.* 484, 102–110.
49. Zorumski C F, Isenberg K E (1991). Insights into the structure and function of GABA0benzodiazepine receptors: ion channels and psychiatry. *Am. J. Psych.*, 148, 162–173.

What is claimed is:

1. A 1H-benz[e]indene dodecahydro compound of the following structural formula:

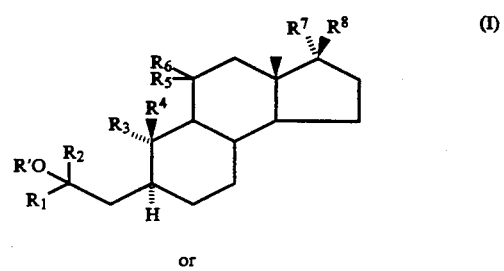

or

-continued

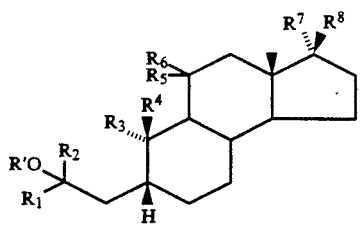
(II)

wherein $R_1$ = H or $C_1$-$C_4$ alkyl or fluoroalkyl;
$R_2$ = H or $C_1$-$C_4$ alkyl or fluoroalkyl, in which $R_1$ and $R_2$ can be the same or different;
$R_3$ = H or $CH_3$;
$R_4$ = H or $CH_3$, in which $R_3$ and $R_4$ can be the same or different;
$R_5$ = H;
$R_6$ = H;
$R_5,R_6$ = =O(carbonyl);
$R_7$ = H;
$R_8$ = a hydrogen bond accepting group.
$R_7,R_8$ = =O(carbonyl); and
R' = H or an ester group,
wherein said ester group (R') is a group derived from reaction between a hydroxyl group with a $C_1$-$C_{18}$ organic acid, acid halide or anhydride, and said hydrogen bond accepting group ($R_8$) is (1) a keton, —CO—R", wherein R" is a $C_1$-$C_4$ alkyl or fluoroalkyl group or a $C_3$-$C_6$ cycloalkyl group, (2) an α-hydroxy ketone, —CO— $CH_2OH$, or ester thereof, —CO—CO$_2$OXOR''', wherein X=C, P=O(OR'''), or S=O, and R''' is a $C_1$-$C_{20}$ alkyl group, (3) an alkyl ester of a carboxylic acid, —COOR" or —$CH_2COOR'''$, wherein R'''is a $C_1$-$C_{20}$ alkyl group, (4) an amine NHR" or N(R")$_2$, wherein R" is a $C_1$-$C_4$ alkyl or fluoroalkyl group or a $C_3$-$C_6$ cycloalklyl group, (5) a nitrile, CN, or a γ-lactone

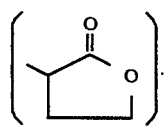

2. A compound of claim 1 having the structure

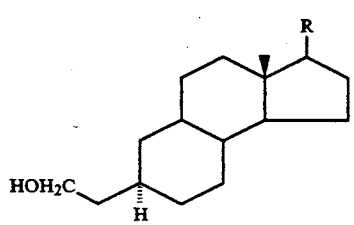

wherein R is =O, CN,

 or $COCH_3$.

3. The compound of claim 2 in which R is =O.
4. The compound of claim 2 in which R is CN.
5. The compound of claim 2 in which R is

6. The compound of claim 2 in which R is $COCH_3$.
7. A compound having the structure

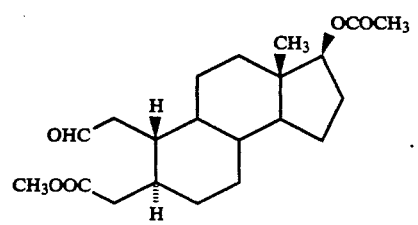

8. A compound having the structure

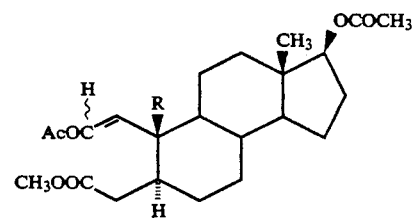

wherein R is H or $CH_3$.

9. A compound having the structure

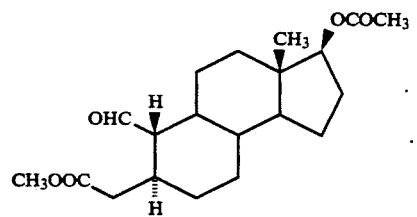

10. A compound having the structure

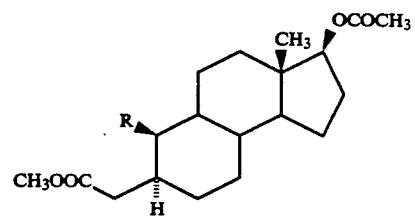

wherein R is H or $CH_3$.

* * * * *

UNITED STATES PATENT AND TRADEMARK OFFICE
CERTIFICATE OF CORRECTION

PATENT NO. : 5,206,415

DATED : April 27, 1993

INVENTOR(S) : Douglas F. Covey, Yuefei Hu and Charles Zorumski

It is certified that error appears in the above-identified patent and that said Letters Patent is hereby corrected as shown below:

Col. 3, line 11, "7" should read --$\gamma$--. Col. 6, line 25, "fluconic" should read --gluconic--. Col. 15, line 46, "1,1Dimethylethyl" should read --1,1-Dimethylethyl--; in line 66, "$C_{361}$" should read --$C_3$--. Col. 16, line 29, after "mixture", insert --was allowed to react at -78°C for 1 h and at room temperature for 1.0 h, then the mixture--; in line 44, after "2918," insert --2850,--; in line 46, "$cm^{-1a}$" should read --$cm^{-1}$--; in line 49, "2.5" should read --2.05--. Col. 17, line 2, "7a$\alpha$" should read --9a$\alpha$--; in line 20, "14.1" should read --15.1--; in line 24, "11.74" should read --11.75--; delete redundant lines 40-60; in line 67, "string" should read --stirring--. Col. 18, line 7, "whased wutg" should read --washed with--; in line 9, "&" should read --%--; in line 19, "69.29" should read --69.20--; in line 39, "7acetic" should read --7-acetic--; in line 46, "gain" should read --again--; in line 64, after 174.09, delete "(OCH=),(=CH), 82.67" and insert --(COOCH$_3$), 171.50(CH$_3$COOCH), 168.32--. Col. 19, line 22, "at 3178°C" should read --to -78°C--; in line 26, "at 3178°C" should read --at -78°C--; in line 34, after "2707," insert --1738,--; in line 40, "C$_3$COO" should read --CH$_3$COO--. Col. 21, line 5, "benz[indene" should read --benz[e]indene--; in line 11, "aw." should read --aq.--. Col. 22, line 22, "10 mg" should read --150 mg--; in line 23, delete "61"; in line 35, "33" should read --3--. Col. 23, line 17, "bringe" should read --brine--. Col. 24, line 28, "7$\alpha$ 9a$\alpha$" should read --7$\alpha$,9a$\alpha$--; in line 29, "(2)" should read --(2- --; in line 44, "200" should read --500--; in line 48, "200" should read --220--. Col. 25, line 29, after "diethyl" insert --ether--.

UNITED STATES PATENT AND TRADEMARK OFFICE
CERTIFICATE OF CORRECTION

PATENT NO. : 5,206,415

DATED : April 27, 1993

INVENTOR(S) : Douglas F. Covey, Yuefei Hu and Charles Zorumski

It is certified that error appears in the above-identified patent and that said Letters Patent is hereby corrected as shown below:

Col. 28, lines 52 and 53, "$Cl^{-1}$" should read --$Cl^{-}$--. Col. 32, in Reference No. 45, "Stude" should read --Study--; in Reference No. 47, "J. Org. Chem., 2729-2731" should read --J. Pharmacol. Exp. Ther., 248, 960-966. Col. 33, Claim 1, line 31, "keton" should read --ketone--; in line 34, "-CO-CO-" should read -- -CO-CH- --.

Signed and Sealed this

Thirtieth Day of May, 1995

Attest:

BRUCE LEHMAN

Attesting Officer

Commissioner of Patents and Trademarks